US007022529B2

(12) United States Patent
Singh et al.

(10) Patent No.: US 7,022,529 B2
(45) Date of Patent: Apr. 4, 2006

(54) PARTICLES FOR DIAGNOSTIC AND THERAPEUTIC USE

(75) Inventors: Sharat Singh, San Jose, CA (US); John S. Pease, Los Altos, CA (US); Jacqueline Sadakian, San Jose, CA (US); Daniel B. Wagner, Sunnyvale, CA (US); Edwin F. Ullman, Atherton, CA (US)

(73) Assignee: Dade Behring Marburg GmbH, Marburg (DE)

( * ) Notice: Subject to any disclaimer, the term of this patent is extended or adjusted under 35 U.S.C. 154(b) by 87 days.

(21) Appl. No.: 10/745,972

(22) Filed: Dec. 24, 2003

(65) Prior Publication Data

US 2004/0241711 A1 Dec. 2, 2004

Related U.S. Application Data

(62) Division of application No. 09/465,065, filed on Dec. 15, 1999, now Pat. No. 6,703,248.

(51) Int. Cl.
*G01N 33/543* (2006.01)

(52) U.S. Cl. .............. 436/518; 436/523; 436/520; 436/524; 436/528; 436/534; 436/535; 436/546; 436/164; 436/172; 436/8; 436/166; 422/82.05; 422/82.07; 422/82.08

(58) Field of Classification Search ........... 436/518, 436/523, 520, 524, 528, 534, 535, 546, 164, 436/172, 8, 166; 422/82.05, 82.07, 82.08
See application file for complete search history.

(56) References Cited

U.S. PATENT DOCUMENTS 3,755,238 A    8/1973  Wiita 3,996,056 A   12/1976  Muller (Continued)

FOREIGN PATENT DOCUMENTS

| EP | 360452 A2 | 9/1989 |
| EP | 369515 A1 | 11/1989 |
| EP | 0 345 776 A2 | 12/1989 |

OTHER PUBLICATIONS

Madison et al; *Brain Research*; 522:1; pp 90-98; Latex Nanosphere Delivery System (LNDS): Novel Nanometer-Sized Carriers of Fluorescent Dyes and active Agents Selectively Target Nuronal Subpopulations via Uptake and Retrograde Transport; Jul. 2, 1990.

(Continued)

*Primary Examiner*—Long V. Le
*Assistant Examiner*—Pensee T. Do
(74) *Attorney, Agent, or Firm*—Theodore J. Leitereg

(57) ABSTRACT

Methods, compositions and kits are disclosed. The compositions are light emitting and comprise a polymeric matrix having dissolved therein a photoactive compound. The composition has the characteristic that, after activation of the photoactive compound, the rate of decrease in the intensity of light emission at any time during a 20-fold decrease in the intensity is proportional to the intensity of the light emission. In one embodiment the polymeric matrix is comprised of particles of about 20 nm to about 100 μm in diameter to which is bound a specific binding pair member. The particles generally comprise a polymeric matrix having dissolved therein about 1 to about 20% by weight of a dopant. The compositions may be used in methods for determining an analyte. A combination is provided comprising (1) a medium suspected of containing the analyte, (2) and the aforementioned composition. The photoactive substance is activated and the effect of the activating on the optical properties of the combination is detected. The presence and amount of the effect is related to the presence and amount of the analyte in the medium. Also disclosed are kits for use in an assay.

7 Claims, 6 Drawing Sheets

U.S. PATENT DOCUMENTS

| | | |
|---|---|---|
| 4,181,636 A | 1/1980 | Fischer |
| 4,264,766 A | 4/1981 | Fischer |
| 4,318,707 A | 3/1982 | Litman et al. |
| 4,388,296 A | 6/1983 | Hart |
| 4,415,700 A | 11/1983 | Batz et al. |
| 4,419,453 A | 12/1983 | Dorman et al. |
| 4,481,136 A | 11/1984 | Khanna et al. |
| 4,483,929 A | 11/1984 | Szoka |
| 4,487,855 A | 12/1984 | Shih et al. |
| 4,650,770 A | 3/1987 | Liu et al. |
| 4,652,533 A | 3/1987 | Jolley |
| 4,699,826 A | 10/1987 | Schwartz et al. |
| 4,719,182 A | 1/1988 | Burdick et al. |
| 4,745,075 A | 5/1988 | Hadfield et al. |
| 4,784,912 A | 11/1988 | Schaeffer et al. |
| 4,801,504 A | 1/1989 | Burdick et al. |
| 4,806,488 A | 2/1989 | Berger, Jr. et al. |
| 4,837,168 A | 6/1989 | De Jaeger et al. |
| 4,891,324 A | 1/1990 | Pease et al. |
| 4,978,625 A | 12/1990 | Wagner et al. |
| 5,053,443 A | 10/1991 | Sutton |
| 5,132,242 A | 7/1992 | Cheung |
| 5,145,774 A | 9/1992 | Tarnowski et al. |
| 5,154,887 A | 10/1992 | Babb et al. |
| 5,157,084 A | 10/1992 | Lee et al. |
| 5,194,300 A | 3/1993 | Cheung |
| 5,234,841 A | 8/1993 | Sutton |
| 5,284,752 A | 2/1994 | Sutton |
| 5,340,716 A | 8/1994 | Ullman et al. |
| 5,489,537 A | 2/1996 | Van Aken |
| 5,545,834 A | 8/1996 | Singh et al. |
| 5,573,909 A | 11/1996 | Singer et al. |
| 5,578,498 A | 11/1996 | Singh et al. |
| 5,618,732 A | 4/1997 | Pease et al. |
| 5,672,478 A | 9/1997 | Singh et al. |
| 5,709,994 A | 1/1998 | Pease et al. |
| 5,716,855 A | 2/1998 | Lerner et al. |
| 5,763,189 A | 6/1998 | Buechler et al. |
| 5,811,311 A | 9/1998 | Singh et al. |
| 5,977,241 A | 11/1999 | Koloski et al. |
| 6,083,602 A | 7/2000 | Caldwell et al. |
| 6,153,299 A | 11/2000 | Smith et al. |
| 6,197,482 B1 | 3/2001 | Lobo et al. |
| 6,211,280 B1 | 4/2001 | Schell |
| 6,255,359 B1 | 7/2001 | Agrawal et al. |
| 6,274,065 B1 | 8/2001 | Deno et al. |
| 6,309,701 B1 | 10/2001 | Barbera-Guillem |

OTHER PUBLICATIONS

O'Connell et al; *Clin Chem*; 31:9; pp 1424-1426; A Highly Sensitive Immunoassay System Involving Anti-Coated Tubes and Liposome-Entrapped Dye; 1985.

PARTICLES FOR DIAGNOSTIC AND THERAPEUTIC USE

This is a DIVISION of application Ser. No. 09/465,065, filed Dec. 15, 1999, now U.S. Pat. No. 6,703,248.

BACKGROUND OF THE INVENTION

1. Field of the Invention

This invention relates to particles for use in assays for analytes, for therapeutic use and for use as pigments. The particles have optical and surface properties that render them more suitable for the aforementioned uses.

The clinical diagnostic field has seen a broad expansion in recent years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

The need to determine many analytes in blood and other biological fluids has become increasingly apparent in many branches of medicine. In endocrinology the knowledge of plasma concentration of a number of different hormones is often required to resolve a diagnostic problem or a panel of markers for a given diagnosis where the ratios could assist in determining disease progression. An even more pressing need is evident in other areas such as allergy testing, the screening of transfused blood for viral contamination or genetic diagnosis.

In other assays such as nucleic acid hybridization assays, there is need to detect and quantify specific target and positive control sequences in a single tube without time consuming separations and transfer steps. In principle internal controls will eliminate the need for a standard curve. Amplification and detection in a single tube without opening the tube also overcomes contamination problems. In mutation analysis, the ability to measure two or more variants in a single tube would allow one to monitor quantitatively the appearance of mutant populations.

Most multi-analyte assays are heterogeneous, have poor sensitivity and poor dynamic range (2 to 100 fold difference in concentration of the analytes is determined) and some require the use of sophisticated instrumentation. A homogeneous assay that has higher sensitivity, large dynamic range ($10^3$ to $10^4$-fold difference in analyte concentration), and fewer and more stable reagents would increase the simplicity and reliability or multianalyte assays.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water-soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labeled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes.

Dyed latex particles have been used previously not only in immunoassays but also for other diverse uses such as photodynamic therapy and as pigments. Both absorptive dyes and dyes that impart fluorescent or chemiluminescent properties have been incorporated into these particles. Frequently, the latex is dyed by dispersing the particles in a solvent that is at least partially organic. The organic solvent causes the particles to swell and is believed to permit the incorporation of increased concentrations of the dyes. While the optical properties of the dyed particles might be expected to be enhanced as more dye is incorporated into the particles this is not necessarily the case. We have observed that increased concentrations of fluorescent dyes tend to promote self-quenching and higher concentrations of absorptive dyes can lead to ground state multimers with different optical properties from the fully dispersed state. Even at low concentrations of chemiluminescent olefins and energy acceptors, we found that the rates of decay of dioxetanes produced in latex particles upon reaction with singlet oxygen are non-linear. This observation was consistent with previously published multiphasic decay of solute excited states in polystyrene films.

2. Brief Description of the Related Art

U.S. Pat. No. 5,340,716 (Ullman, et al.) describes an assay method utilizing photoactivated chemiluminescent labels.

Photoactivatable chemiluminescent matrices are described in U.S. Pat. No. 5,709,994 (Pease, et al.).

U.S. Pat. No. 5,194,300 (Cheung 1) discusses methods of making fluorescent microspheres.

U.S. Pat. No. 5,132,242 (Cheung 2) discusses fluorescent microspheres and methods of using them.

U.S. Pat. No. 4,837,168 (de Jaeger) discloses an immunoassay using colorable latex particles.

U.S. Pat. No. 4,699,826 (Schwartz, et al.) discusses fluorescently labeled microbeads.

Madison, et al., describes latex nanosphere delivery system (LNDS), novel nanometer-sized carriers of fluorescent dyes and active agents selectively target neuronal subpopulations via uptake and retrograde transport in Brain Research (1990) 522:90–98.

U.S. Pat. No. 3,996,056 (Muller) discusses diazotype reproduction layer formed from matrix of spheric particle polystyrene pigment and diazotype components.

U.S. Pat. No. 3,755,238 (Wiita) discloses high gloss and low block coating composition containing plasticized vinyl resin latex and finely divided polyolefin particles.

O'Connell, et al., describe a highly sensitive immunoassay system involving antibody-coated tubes and liposome-entrapped dye in Clin. Chem. (1985) 31(9):1424–1426.

U.S. Pat. No. 5,618,732 (Pease, et al. 1) discusses a method of calibration with photoactivatable chemiluminescent matrices.

U.S. Pat. No. 5,489,537 (Van Aken) discloses agglutination assays and kits employing colloidal dyes.

U.S. Pat. No. 5,284,752 (Sutton 1) discusses methods of preparing a polymeric latex composition and water-insoluble biological reagent.

U.S. Pat. No. 5,234,841 (Sutton 2) discusses methods of preparing a polymeric latex composition and water-insoluble biological reagent.

U.S. Pat. No. 5,157,084 (Lee, et al.) discusses a process of making hollow polymer latex particles.

U.S. Pat. No. 5,053,443 (Sutton 3) discloses methods of preparing a polymeric latex composition and water-insoluble biological reagent.

U.S. Pat. No. 4,891,324 (Pease) discloses a particle with luminescer for assays.

U.S. Pat. No. 4,801,504 (Burdick, et al.) discusses fluorescent labels having a polysaccharide bound to polymeric particles.

U.S. Pat. No. 4,784,912 (Schaeffer, et al.) discusses latex particles incorporating stabilized fluorescent rare earth labels.

U.S. Pat. No. 4,650,770 (Liu, et al.) discloses energy absorbing particle quenching in light emitting competitive protein binding assays.

U.S. Pat. No. 4,483,929 (Szoka) discusses liposomes with glycolipid-linked antibodies.

U.S. Pat. No. 4,388,296 (Hart) discloses energy-emitting latex particulates.

U.S. Pat. No. 4,318,707 (Litman, et al.) discusses macromolecular fluorescent quencher particle in specific receptor assays.

U.S. Pat. No. 4,264,766 (Fischer) discloses immunological diagnostic reagents.

Latex particles in analytical reagents, elements and methods is discussed in European Patent Application 0 360 452 A2 (Warshawsky, et al.).

Aqueous suspension for diagnostic tests is discussed in European Patent Application 0 369 515 A1 (Brouwer).

U.S. Pat. No. 5,573,909 (Singer, et al.) discloses fluorescent labeling using microparticles with controllable Stokes shift.

Hydrophilic latex particles and use thereof is discussed by Batz, et al., in U.S. Pat. No. 4,415,700.

Colored latex and methods for making the same and colored finely divided products are discussed in U.S. Pat. No. 4,487,855 (Shih, et al.).

U.S. Pat. No. 4,419,453 (Dorman, et al.) discloses immunological agglutination assays with dyed or colored latex and kits.

U.S. Pat. No. 4,745,075 (Hadfield, et al.) discusses diagnostic test methods.

A process for producing immunological diagnostic reagents is discussed in U.S. Pat. No. 4,181,636 (Fischer).

U.S. Pat. No. 5,716,855 (Lerner, et al.) discloses fluorescent latex containing at least two fluorochromes, process for producing it and application thereof.

SUMMARY OF THE INVENTION

One aspect of the present invention is a light emitting composition comprising a polymeric matrix having dissolved therein a photoactive compound. The composition has the characteristic that, after activation of the photoactive compound, the rate of decrease in the intensity of light emission from the composition at any time during a 20-fold decrease in the intensity is proportional to the intensity of the light emission. In one embodiment the polymeric matrix is comprised of particles of about 20 nm to about 100 μm in diameter.

Another aspect of the present invention is a light emitting composition comprising particles of about 20 to about 100 μm in diameter. The particles comprise a polymeric matrix having dissolved therein (a) about 1 to about 20% by weight of a dopant and (b) a photoactive compound. The light emitting composition is characterized in that, following cessation of activation of the photoactive compound, the rate of decrease in the intensity of light emission from the polymeric matrix at any time during a 20-fold decrease in the intensity is proportional to the intensity of the light emission.

Another aspect of the present invention is a method for determining an analyte. A combination is provided comprising (1) a medium suspected of containing the analyte, (2) a first specific binding pair (sbp) member capable of binding to the analyte or to a second sbp member to form a complex related to the presence of the analyte, wherein at least one of said sbp members is bound to polymeric particles of about 20 nm to about 100 μm in diameter having homogeneously dispersed therein about 1 to about 20 weight percent of a dopant and a photoactive substance. The photoactive substance is activated and the effect of the activating on the optical properties of the combination is determined. The magnitude of the effect is related to the amount of the analyte in the medium.

Also included with the scope of the present invention is a kit for use in an assay. The kit comprises in packaged combination reagents for conducting an assay. The reagents comprise at least one member of a specific binding pair bound to polymeric particles of about 20 nm to about 100 μm in diameter having incorporated therein about 1 to about 20 weight percent of a dopant and a photoactive substance.

DESCRIPTION OF THE SPECIFIC EMBODIMENTS

Figure 1:
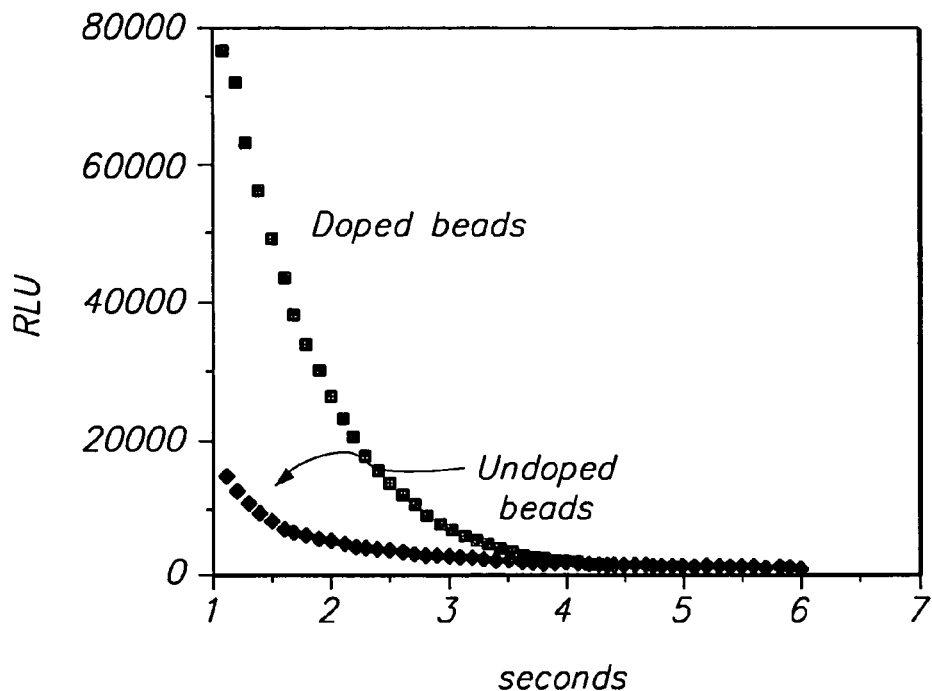
FIG. 1 is a graph showing a plot of signal intensity versus time for particles in accordance with the present invention and particles of the prior art.

We have found that dyes incorporated in polystyrene latex particles behave more like their solutions in non-viscous organic solvents if dopants are also incorporated in the particles. Incorporation of the dopants provides a number of important advantages not only for immunoassays but also for other types of assays and in other uses of these particles. With chemiluminescent particles we found that the emission decay rates now followed practically perfect first order kinetics. This provided higher initial light intensities, which translated into a higher signal to background ratio and improved detectability. It also made it possible to deconvolute signals with different decay rates from one another.

The particles of the present invention are more effectively coated with aminodextran. Thus, a particle of the invention takes up 10±2% aminodextran compared to 4±1% for known particles. Better surface coverage of particles with aminodextran leads to isotropic surfaces for the particles, which in turn leads to better assay results.

The compositions of the invention provide for solution-like chemical behavior such as, for example, in the reaction with of components with singlet oxygen, in chemiluminescence decay or fluorescence decay and in concentration effects.

Introduction of dopants into sensitizer particles also provided improvements. The rate of singlet oxygen formation upon irradiation of sensitizer particles does not increase linearly with the amount of sensitizer in the particles. Instead the rates reach a plateau and with addition of enough sensitizer the rate of singlet oxygen formation actually falls off. Without wishing to be limited to any particular mechanism, one reason for this may be self-quenching or stacking of sensitizers such as, for example, di-(tri-n-hexylsilyl)-t-butyl silicon phthalocyanine and di-(tri-n-hexylsilyl)-silicon napthalocyanine, in particles. It is believed that adding of plasticizer prevents dyes from stacking or self-quenching thus increasing singlet oxygen production. When a dopant is included in the particles, more sensitizer can be incorporated into the particles before this plateau is reached.

One advantage of increased singlet oxygen production in assays is that a lower light intensity can be used to produce the same amount of singlet oxygen and thus the same intensity of chemiluminescence. This reduces chemiluminescent background from unwanted sources and also reduces the cost of instrumentation. Alternatively, the light intensity can remain unchanged and the increase rate of singlet oxygen production can be used to increase the sensitivity of the assays.

Increasing the efficiency of singlet oxygen production per particle also provides an improvement for applications to photodynamic therapy. More singlet oxygen can be delivered for each particle that binds to diseased tissue and/or less damaging lower laser power can be used.

Before proceeding further with a description of the specific embodiments of the present invention, a number of terms will be defined and described in detail.

Component—component of interest; the compound or composition to be detected. The component may be an analyte, a reference compound, a control compound, a calibrator, and the like.

Analyte—the analyte is a substance to be detected or its concentration determined and frequently is a member of a specific binding pair (sbp). It may be a ligand, which is monovalent (monoepitopic) or polyvalent (polyepitopic), usually antigenic or haptenic, and may be a single compound or plurality of compounds which share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus. When not a member of a sbp the analyte may be an enzyme, an enzyme substrate, or any other substance, usually of clinical significance, that is capable of being detected by its intrinsic ability to absorb light or by its ability to change the concentration of a substance with an ability to absorb light such as creatine, cholesterol, urea, alkaline phosphatase, potassium, triglycerides, and the like.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g., phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs is the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The biological tissue includes excised tissue from an organ or other body part of a host and body fluids, for example, urine, blood, plasma, serum, saliva, semen, stool, sputum, cerebral spinal fluid, tears, mucus, and the like.

Label reagent—a reagent for use in conducting an assay for one or more components. The label reagent generally also comprises a member of a specific binding pair.

Photoactive compound—a compound which alone or in combination with another compound can be photoactivated by absorption of light having wavelengths between 300 and 1200 nm, preferably between 450 and 900 nm, frequently between 600 and 900 nm. Photoactivation produces an irreversible chemical change in one or both of said compounds. Photoactive compounds of this invention preferably act in combination with another compound wherein one of the compounds absorbs light and the other compound thereupon undergoes an irreversible chemical change. Such photoactive compounds include chemiluminescent compounds, photosensitizers, photoactivatable fluorescent compounds, and the like. The photoactive compounds are incorporated into a polymeric matrix and are therefore chosen to be hydrophobic and very much more soluble in the matrix in water, usually at least $10^3$ times and preferably at least $10^8$ as soluble in the matrix as in water.

Olefins capable of reacting with singlet oxygen—a typical reaction of olefins with singlet oxygen is 2+2 addition to form a dioxetane. Suitable olefins usually have no saturated C—H group attached to an olefinic carbon except unreactive bridgehead carbons and will preferably have one or more electrons donating groups directly attached to the olefinic carbon or in conjugation with the olefin. Dioxetanes can dissociate spontaneously or by heating with spontaneous chemiluminescence, or the carbonyl groups that are formed can be formed as part of a fluorescent group or be capable of undergoing subsequent reactions that lead to a fluorescent molecule. Alternatively, this dissociation reaction can lead to separation of a quenching group from a fundamentally fluorescent group that thereby regains its fluorescent property.

Another type of reaction of singlet oxygen with olefins is 4+2 cycloaddition with dienes, usually aromatic compounds such as naphthalenes, anthracenes, oxazoles, furans, indoles, and the like. Such a reaction leads initially to an endoperoxide. In some cases endoperoxides can rearrange to active esters or anhydrides that are capable of reaction with a suitably placed group to provide a lactone or lactam that can be fluorescent. Alternatively, the endoperoxides may oxidize a fluorescent or chemiluminescent compound precursor. Endoperoxides can also dissociate spontaneously or on heating with chemiluminescent emission or oxidize a fluorescent leuco dye.

Still another type of reaction of singlet oxygen with olefins is the "ene" reaction that produces an allylhydroperoxide. Suitable olefins have a reactive saturated C—H attached to an olefinic carbon. The allylhydroperoxide product can react with an active ester in the same molecule to form a dioxetanone that can spontaneously or by heating dissociate with chemiluminescent emission.

In general, olefins of interest are those that undergo a chemical reaction upon reaction with singlet oxygen to form a metastable reaction product, usually a dioxetane or endoperoxide, which is capable of decomposition with the simultaneous or subsequent emission of light, usually within the wavelength range of 250 to 1200 nm. Preferred are electron rich olefins usually containing electron-donating groups. Exemplary of such electron rich olefins are enol ethers, enamines, 9-alkylidene-N-alkylacridans, arylvinylethers, 1,4-dioxenes, 1,4-thioxenes, 1,4-oxazines, arylimidazoles, 9-alkylidene-xanthanes and lucigenin.

The luminescence, either chemiluminescence or fluorescence, produced upon reaction of the olefins of interest with singlet oxygen will preferably be at wavelengths above 300 nanometers (nm), preferably above 500 nanometers, and more preferably above 550 nm. Compounds that absorb light at wavelengths beyond the region where the sample components contribute significantly to light absorption will be of particular use in the present invention. The absorbance of serum drops off rapidly above 500 nm and becomes insignificant above 600 nm. Luminescence above 550 nm is of particular interest. However, luminescence at shorter wavelengths is useful when interference from absorbance of the sample is absent. Preferably, the olefins capable of reacting with singlet oxygen will absorb light at less than about 400 nm to permit convenient handling in room light without the risk of inadvertently producing singlet oxygen by photosensitization.

Chemiluminescent compounds (chemiluminescer)—Frequently a chemiluminescent photoactive compound. Examples of chemiluminescers, by way of illustration and not limitation, are e.g., olefins capable of reacting with singlet oxygen or a peroxide, to form hydroperoxides or dioxetanes, which can decompose to ketones or carboxylic acid derivatives; stable dioxetanes which can decompose by the action of_light; acetylenes which can react with singlet oxygen to form diketones; hydrazones or hydrazides that can form azo compounds or azo carbonyls such as luminol, aromatic compounds that can form endoperoxides, etc. As a consequence of the activation reaction, the chemiluminescers directly or indirectly cause the emission of light.

Examples of suitable electron rich chemiluminescent olefins are set forth in U.S. patent application Ser. No. 07/923, 069 at page 64, line 8, to page 76, line 11, the disclosure of which is incorporated herein by reference. Such olefins generally have an electron-donating group in conjugation with the olefin.

The dioxetanes may be luminescent alone or in conjunction with a fluorescent energy acceptor. Enol ethers are examples of such olefins. Frequently, the enol ether compounds will have at least one aryl group bound to the olefinic carbons where the aryl ring is substituted with an electron donating group at a position that increases the reactivity of the olefin to singlet oxygen and/or imparts fluorescence to the product of dissociation of the resultant dioxetane. The electron-donating group can be, for example, hydroxyl, alkoxy, disubstituted amino, alkyl thio, furyl, pyryl, etc. Preferably, the enol ethers have an electron-donating group bound directly to an olefinic carbon.

Enamines are another example of such olefins. In general, useful enamines will be governed by the rules set forth above for enol ethers.

Another family of chemiluminescers is the 2,4,5-triphenylimidazoles, with lophine as the common name for the parent product. Chemiluminescent analogs include para-dimethylamino and -methoxy substituents.

Other chemiluminescent olefins that satisfy the requirements given above may be found in European Patent Application No. 0,345,776.

The chemiluminescent composition in the present invention is generally associated with a polymeric matrix within a particle. As used herein, the term "associated with" means dissolution in the polymeric matrix.

Photoactivatable fluorescent compounds—Examples of photoactivatable fluorescent compounds, by way of illustration and not limitation, are e.g., olefins capable of reacting with singlet oxygen and hydrazides, and hydrazones that react with singlet oxygen or a peroxide with simultaneous or subsequent cleavage of a bond to yield fluorescent compounds. Examples of photoactivatable fluorescent compounds are given in U.S. Pat. No. 5,616,719, which is hereby incorporated by reference. In general leuco fluorescent dyes, particularly dihydromerocyanine dyes, are useful in that they can be readily oxidized by singlet oxygen to give fluorescent compounds.

Sensitizer—a molecule, usually a compound, for generation of a reactive intermediate, frequently singlet oxygen, or for activation of a photoactive compound. Preferably, the sensitizer is a photosensitizer. However, other sensitizers can be chemi-activated (e.g., enzymes and metal salts) including, by way of example and not limitation, other substances and compositions that can produce singlet oxygen with or, less preferably, without activation by an external light source. Thus, for example, molybdate ($MoO_4^=$) salts and chloroperoxidase and myeloperoxidase plus bromide or chloride ion (Kanofsky, J. Biol. Chem. (1983) 259:5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagent, chloroperoxidase is bound to a surface and molybdate is incorporated in the aqueous phase of a liposome. Also included within the scope of the invention as photosensitizers are compounds that are not true sensitizers but which on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

Photosensitizer—a sensitizer for activation of a photoactive compound, frequently by the generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200–1,100 nm, usually, 300–1,000 nm, preferably, 450–950 nm, with an extinction coefficient at its absorbance maximum greater than 500 $M^{-1}$ $cm^{-1}$, preferably, 5,000 $M^{-1}$ $cm^{-1}$, more preferably, 50,000 $M^{-1}$ $cm^{-1}$, at the excitation wavelength. The lifetime of an excited state produced following absorption of light in the absence of oxygen will usually be at least 100 nanoseconds, preferably, at least 1 millisecond. In general, the lifetime must be sufficiently long to permit energy transfer to a chemiluminescer or to_oxygen, which will normally be present at concentrations in the range of $10^{-5}$ to $10^{-3}$ M depending in the medium. The photosensitizer excited state will usually have a different spin quantum number (S) than its ground state and will usually be a triplet (S=1) when the ground state, as is usually the case, is a singlet (S=0). Preferably, the photosensitizer will have a high intersystem crossing yield. That is, photoexcitation of a photosensitizer will usually produce a triplet state with an efficiency of at least 10%, desirably at least 40%, preferably greater than 80%.

Photosensitizers will be relatively photostable and, preferably, will not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N. F. Turro, "Molecular Photochemistry" page 132, W. A. Benjamin Inc., N.Y. 1965.

The photosensitizers are preferably relatively non-polar to assure dissolution into a lipophilic member when the photosensitizer is incorporated in a latex particle.

Latex particles—latex particles having an average diameter of at least about 20 nm and not more than about 100 microns, usually at least about 40 nm and less than about 20 microns, preferably, from about 0.10 to 2.0 microns average diameter, spherical or non-spherical, preferably spherical. The particles may have any density, but will preferably have a density approximating water, generally from about 0.7 to about 1.5 g/ml. The particles may or may not have a charge, and when they are charged, they are preferably negative. When used in binding assays they will frequently also be adsorptive or functionalizable so as to bind or attach at their surface, either directly or indirectly, an sbp member.

"Latex" signifies a particulate water suspendable water insoluble polymeric material. The latex is frequently a substituted polyethylene such as polystyrene-butadiene, polyacrylamide, polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, polyvinyl chloride, polyvinyinaphthalene and the like. In general the latex particle composition is chosen so as to favor association of the photoactive compound with the polymeric matrix. For this reason the polymers will usually be linear polymers. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photoactive compound with latex particles utilized in the present invention may involve incorporation during formation of the particles by polymerization but will usually involve incorporation into preformed particles, usually by noncovalent dissolution into the particles. Photoactive compounds are therefore chosen that will dissolve in the polymeric matrix and are therefore usually hydrophobic, and the latex particle composition is chosen so as to favor association of the photoactive compound with the polymeric matrix. Usually, a solution of the photoactive compound will be employed. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the label compounds into the particles and are particularly suitable. The solvents may be used singly or in combination. Solvents should be selected that can be fully removed from the particles or that do not interfere with photoactivation. Frequently, hydroxylic solvents are also preferred. Typical aromatic cosolvents including dibutylphthalate, benzonitrile, naphthonitrile, dioctylterephthalate, dichlorobenzene, diphenylether, dimethoxybenzene, etc, will be used at sufficiently low concentrations to avoid dissolution of the particles but at sufficient concentrations to swell the particles.

Generally, the temperature employed during the procedure will be chosen to maximize the ability of light to activate the photoactive compound with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded or attached to the particle in a manner similar to that discussed above with respect to other matrices.

Binding of sbp members to the latex particles may be direct or indirect, covalent or non-covalent and can be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface of the latex particles will usually be polyfunctional or be capable of being polyfunctionalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The length of a linking group to an oligonucleotide or sbp member may vary widely, depending upon the nature of the compound being linked, the effect of the distance between the compound being linked and the surface on the specific binding properties and the like.

The photoactive compounds are incorporated into the polymeric matrix either during or after the preparation of the polymeric matrix. They are chosen to dissolve in the matrix hydrophobic to reduce their ability to dissociate from the polymeric matrix. In general the polymeric matrix latex particle composition is chosen so as to favor association of the photoactive compound with the polymeric matrix.

The amount of photoactive compound incorporated into the polymeric matrix in the compositions of the invention depends upon a number of factors such as the nature of the photoactive compound and the polymeric matrix and the intended use of the resulting reagent. The photoactive compound is present in the polymeric matrix in an amount necessary to maximize the efficiency of light to cause photoactivation. In an assay the degree of photoactivation will be equivalent to the magnitude of the signal produced in accordance with the invention, i.e., to provide the highest signal to background in an assay. In, for example, photodynamic therapy the degree of photoactivation will be equivalent to the amount of singlet oxygen produced. Generally, the amount of photoactive compound is determined empirically and is usually about from $10^{-8}$ to 1M, preferably, from $10^{-5}$ to $10^{-2}$ M, more preferably, $10^{-3}$ to $10^{-1}$ M.

In general, the sbp member will be present in from about 0.5 to 100, more usually 1 to 90, frequently from about 5 to 80 and preferably from about 50 to 100 mole percent of the molecules present on the surface of the latex particles. The particular amount of sbp member is also dependent on a number of factors and is usually best determined empirically.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond that links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur, halogen (chlorine, bromine, iodine, fluorine) and phosphorus, and which may or may not be bound to one or more metal atoms.

Electron-donating group—a substituent which, when bound to a molecule, is capable of polarizing the molecule such that the electron-donating group becomes electron poor and positively charged relative to another portion of the molecule, i.e., has reduced electron density. Such groups include, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur, halogen and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxyl groups (carboxylic acids), hydroxyl groups (alcohols), mercapto groups (thiols), carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes and nitriles, and alkyl, alkylidine, aryl, aralkyl, and alkyl, aryl, and aralkyl substituted with one or more of the aforementioned functional groups, e.g., phenyl, naphthyl, phenanthryl, m-methoxyphenyl, dimethylamino, trityl, methoxy, N-morpholino and may be taken together to form a ring such as, for example, adamantyl, N-methyacridanylide, xanthanylidine, 1-(3,4-benzo-5-hydrofurylidene), and the like.

Linking group—a group involved in the covalent linkage between molecules. The linking group will vary depending upon the nature of the molecules, i.e., label, matrix, sbp member or molecule associated with, or part of, a particle being linked. Functional groups that are normally present or are introduced on a latex particle or an sbp member will be employed for linking these materials.

For the most part, carbonyl functionalities will find use, both oxocarbonyl, e.g., aldehyde, and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference in its entirety.

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described above for the substituent having from 1 to 50 atoms. As a general rule, the length of a particular linking group can be selected arbitrarily to provide for convenience of synthesis and the incorporation of any desired group such as an energy acceptor, fluorophor, group for analysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α,β-unsaturated ester. These functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettability of solids with water and the solubility in water of compounds to which it is bound. Such functional group or functionality can be a substituent having 1 to 50 or more atoms and can include a group having a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO—(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of an sbp member or the like to a particulate composition comprised of the label.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic. Lipophilic groups usually comprise plasticizers and may also be bonded to a label or other substance to increase its solubility in a non-aqueous matrix.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

As mentioned above, one aspect of the present invention is a light emitting composition comprising a polymeric matrix having dissolved therein a photoactive compound. The composition has the characteristic that, after activation of the photoactive compound, the rate of decrease in the intensity of light emission from the polymeric matrix at any time during a 20-fold decrease in the intensity (exponential decay) is proportional to the intensity of the light emission. This is usually achieved by incorporating into the matrix a sufficient amount of a dopant such as about 0.1 to about 25%, usually about 1 to about 20%, more usually, about 2 to about 15%, by weight of a dopant.

The dopant may be any organic compound that is non-polar, usually water insoluble and relatively flexible provided that it is sufficiently soluble in the latex to prevent leaching out at an appreciable rate in the presence of any detergents of other lipophilic substances that may come into contact with the particles during their period of use or storage. As a general rule, the distribution in favor of the matrix must be so high that the dopant is kinetically substantially prevented from escaping. Such distribution avoids leaching of the dopant when a hydrophobic substance is included in the aqueous medium. In general, dopants of use in this invention will be at least $10^{10}$, frequently at least $10^{14}$, and preferably at least $10^{18}$ times as soluble in the polymer matrix as in water.

Dopants that are preferred in the present compositions include plasticizers, such as higher alkylaromatic and higher alkyloxyaromatic compounds and fluorocarbons. By "higher alkyl" is meant a branched or unbranched saturated monovalent hydrocarbon radical containing at least 10 carbon atoms, usually 10 to 30 carbon atoms, more usually, 15 to 25 carbon atoms. Exemplary of such radicals are decyl, undecyl, dodecyl, tridecyl, tetradecyl, pentadecyl, hexadecyl, heptadecyl, octadecyl, nonadecyl, eicosyl, 4-methyl-3,3-diethyl-5-isopropyloctane, 4-t-butyl-4-isopropyldecane, and the like. The aromatic moiety of the plasticizer is one that is generally characterized as being capable of undergoing substitution reactions. Such compounds are typically cyclic compounds having one or more double bonds. Usually, the compounds contain one or more five-, six- or seven-membered rings. The aromatic compounds may contains only hydrogen and carbon or they may be heterocyclic and contain, besides hydrogen and carbon atoms, one or more atoms such as nitrogen, oxygen, sulfur, and the like. One group of aromatic moieties comprises those that contain only carbon and hydrogen such as, for example, benzene, naphthalene, anthracene, phenanthrene, biphenyl, and the like, which may be substituted with one or more substituents. Other moieties include, for example, pyridyl, pyrrolyl, furyl, quinolyl, phenanthrolyl, acridyl and the like. Particular examples of plasticizers, by way of illustration and not limitation are heptadecylbenzene, dodecyloxynaphthalene, bis-hexadecylnaphthalene, and chlorophenyloctadecane.

The fluorocarbons are compounds comprising carbon atoms and fluorine atoms. In general, the fluorocarbons comprise about 1 to about 20, usually, about 2 to about 10, fluorine atoms and about 5 to about 30, usually, about 10 to about 20, carbon atoms. The carbon atoms may be part of an aromatic compound. Particular compounds include condensed aromatics such as, e.g., decahydronaphthalene, dodecahydroanthracene, tetradecahydrophenanthrene, etc., biphenyl, and the like, which are fluorinated with one or more fluorine atoms. Particular examples of fluorocarbons, by way of illustration and not limitation, include perfluoronaphthalene (perfluorodecalin), perfluoroanthracene, perfluorophenanthrene, and so forth.

The plasticizer is incorporated into the particles usually after the photoactive substance has been incorporated therein. Alternatively the plasticizer is incorporated into the particle after incorporation of the photoactive compound. To incorporate the plasticizer the particles are heated in an organic solvent in which the particles are substantially insoluble and in which the photoactive substance has limited solubility. Such organic solvents include by way of example and not limitation, ethoxyethanol, ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane, and the like and about 1% to about 80% aqueous mixtures thereof.

In a less preferred embodiment the plasticizer may be incorporated during the dyeing process; however, aggregation may occur and thus this approach is not preferred and may be used only when such aggregation may be tolerated. When the plasticizer is incorporated during the incorporation of the photoactive compound, it is included in the solution of for the incorporation as described above.

The plasticizer is included in the solvent in an amount so that the desired level of plasticizer will be present in the resulting particles. The amount of plasticizer in the solvent is dependent on the nature of the solvent and the nature of the particles as well as that of the plasticizer. Usually, the plasticizer concentration is about 0.1% to about 25%, preferably, about 2% to about 15%, more preferably 3% to 7%. The solvent is heated at a temperature of about 40 to about 180° C., usually, about 60 to about 140° C., for a period of about 20 minutes to about 10 hours, usually, about 1 hour to about 6 hour.

It is sometimes desirable to include in the solvent an agent, usually a polymer that prevents the aggregation of the particles, particularly when the solvent is partially aqueous. The agent chosen is dependent on the nature of the solvent and of the particles. Examples of such agents by way of illustration and not limitation are dextran, aminodextran, albumin, polyvinyl alcohol, starch, polylysine, polyacrylic acid, and the like. The amount of such an agent is that which will be effective in reducing or eliminating aggregation of the particles. Such an amount is usually about 0.1% to about 20%, preferably, about 0.5% to about 5% by weight.

One embodiment of the present invention is directed to a method for preparing particles comprising a polymeric matrix having dissolved therein a photoactive compound and about 0.1% to about 25%, preferably, about 2% to about 10%, by weight of a plasticizer. The particles have a diameter of about 20 to about 100 μm. The method comprises heating a mixture comprising (i) the particles comprising the photoactive compound and (ii) the plasticizer in an aqueous medium for a period of time and at a temperature and concentration sufficient for about 1% to about 20%, preferably, about 2% to about 15%, by weight of the plasticizer to become dissolved in the particles. This alternative preparation of plasticizer particles involves heating a mixture of dyed particles and plasticizer in an aqueous medium such as an aqueous organic solvent. Subsequently, the plasticized particles can be reacted with a reagent to provide a dextran coating on the particles. Such a reagent includes, for example, iodoaminodextran and the like in the presence of a coupling agent such as EDAC and the like to yield plasticizer particles with an aminodextran coating. This approach to the preparation of plasticizer particles permits the use of a more stable reagent such as iodoaminodextran and the like for forming the aminodextran coating. The preparation of plasticizer particles exemplified in Example 1 involves combining the dyed particles with plasticizer and aminodextran in an aqueous medium and heating the combination in the presence of a coupling agent such as EDAC.

As mentioned above, with the chemiluminescent particles we found that the emission decay rates now followed practically perfect exponential kinetics. This provided higher initial light intensities, which translated into a higher signal to background ratio and improved detectability. It also made it possible to deconvolute signals with different decay rates from one another. A comparative experiment using plasticizer (heptadecylbenzene)-doped and undoped chemiluminescer particles in a hepatitis B antigen immunoassay showed an approximate 2.3-fold increase in sensitivity (i.e., the slope of the response curve) at 1 pg/ml, which translated into a 4-fold increase in detectability (from 5 down to 1 pg/ml where the detection limit was defined as a signal that was 2.3 standard deviations higher than a negative).

With regard to sensitizer particles, when a dopant is included in the particles, more sensitizer can be incorporated into the particles before the increase in the rate of singlet oxygen with increased sensitizer concentration reaches a plateau. In one experiment the rate of singlet oxygen production was increased by 2.2-fold when heptadecylbenzene was incorporated into latex particles containing a phthalocyanine photosensitizer. Singlet oxygen production was measured by irradiation of a sensitizer particle suspension in a solution of 9,10-bis-carboxyethylanthracene and subsequently measuring the resulting decrease in the 9,10-bis-carboxyethylanthracene concentration by removing the particles and measuring the absorbance of the solution.

As mentioned above, the present compositions have particular application in the area of assays. One aspect of the present invention is, therefore, a method for determining an analyte. A combination is provided comprising (1) a medium suspected of containing the analyte, (2) a first specific binding pair (sbp) member capable of binding to the analyte or to a second sbp member to form a complex related to the presence of the analyte, and (3) polymeric particles of about 20 nm to about 100 μm in diameter having homogeneously dispersed therein about 1 to about 20 weight percent of a dopant and a photoactive compound. The photoactive compound is activated and the effect of the activating on the optical properties of the combination is detected. The presence and amount of the effect is related to the presence and amount of the analyte in the medium.

The assay is usually carried out in an aqueous buffered medium at a moderate pH, generally that which provides optimum assay sensitivity. The aqueous medium may be solely water or may include from 0.01 to 80 or more volume percent of a cosolvent. The pH for the medium will usually be in the range of about 4 to 13, more usually in the range of about 5 to 10, and preferably in the range of about 6.5 to 9.5. The pH is generally selected to achieve optimum assay sensitivity and specificity. Among the factors that must be considered are the pH dependence of the rates of the reactions involved, the binding of binding members and the minimization of non-specific binding, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement. Incubation temperatures will normally range from about 5° to 99° C., usually from about 15° to 70° C., more usually 20 to 45° C. Temperatures during measurements will generally range from about 10° to 70° C., more usually from about 20° to 45° C., more usually 20° to 25° C.

In some instances the photoactivated fluorescent or chemiluminescent compounds may require heating up to 100° C. in order to decay to produce fluorescence or chemiluminescence because the product of its reaction is relatively stable at ambient temperatures. Relatively stable dioxetanes can be formed, for example, by reaction of singlet oxygen with adamantylidenes (see, e.g., McCapra, supra) and relatively stable endoperoxides can be formed by reaction of singlet oxygen with 1,4-disubstituted naphthalenes and anthracenes (see, e.g., N.J. Turro, Modern Molecular Photochemistry (1978) Benjamin Cummings Publishing Co. page 594). In both circumstances above, the stable materials will undergo decay upon heating, usually, at a temperature of less than 200° C., preferably about 50 to 100° C. Such heating causes the rapid decomposition of the singlet oxygen/olefin adduct and thus, where chemiluminescence is produced, the emission of light occurs over a short period of time. The use of this approach may be desirable when separate signals from different fluorescent or chemiluminescent compounds are difficult to fully resolve by lifetime and wavelength.

The concentration of components to be detected will generally vary from about $10^{-5}$ to $10^{-21}$ M, more usually from about $10^{-6}$ to $10^{-14}$ M. Considerations, such as whether the assay is qualitative, semiquantitative or quantitative, the particular detection technique and the nature and concentration of the component of interest will normally determine the concentrations of the various reagents.

While the concentrations of the various reagents in the assay medium will generally be determined by the concentration range of interest of the components to be detected, the final concentration of each of the reagents will normally be determined empirically to optimize the sensitivity of the assay over the range. That is, a variation in concentration of the components to be detected that is of significance should provide an accurately measurable signal difference.

While the order of addition may be varied widely, there will be certain preferences depending on the nature of the assay. The simplest order of addition is to add all the materials simultaneously. Alternatively, the reagents can be combined wholly or partially sequentially. One or more incubation steps may be involved after the reagents are combined, generally ranging from about 30 seconds to 6 hours, more usually from about 2 minutes to 1 hour.

The luminescence or light produced by the present compositions comprising a chemiluminescent or fluorescent compound can be measured visually, photographically, actinometrically, spectrophotometrically or by any other convenient means to determine the amount thereof, which is related to the amount of each component in the medium.

The method and compositions of the invention may be adapted to most assays involving sbp members such as ligand-receptor, e.g., antigen-antibody reactions, polynucleotide binding assays, and so forth. The assays are usually homogeneous or heterogeneous, preferably homogeneous, including competitive and sandwich. In a specific binding assay, the sample may be pretreated, if necessary, to remove unwanted materials.

As mentioned previously, the first sbp member above is capable of binding to the analyte or to a second sbp member capable of binding to the analyte. When the second sbp member is also capable of binding to the analyte, a sandwich assay protocol can result. The immunological reaction for a sandwich type assay usually involves an sbp member, e.g., an antibody, that is complementary to the analyte, a second sbp member, e.g., antibody, that is also complementary to the analyte and bound to the particulate matrix, and the sample of interest.

One of the sbp members alternatively can be analogous to the analyte, in which case a competitive assay protocol can result. The immunological reaction for a competitive protocol usually involves an sbp member that is complementary to the analyte and an sbp member that is analogous to, usually a derivative of, the analyte. One of these sbp members will be associated with the matrix.

In one type of assay, a sample suspected of containing an analyte, which is an sbp member and the other assay components are combined with a particulate matrix of the present invention. The medium is then irradiated and subsequently examined for the presence of spontaneous (i.e., chemiluminescent) or light induced (i.e., fluorescent) emission, usually by measuring the amount of light emitted, which is related to the amount of analyte in the sample. This approach is a homogeneous assay where a separation step is not employed.

A typical assay protocol is described next by way of example and not limitation. A chemiluminescent particle composition of the present invention is attached to a specific binding reagent (for example: antibody, oligonucleotide, receptor, etc.) that is complementary to the analyte. A sensitizer particle is attached to a second specific binding reagent that is complementary to the analyte. In a sandwich assay format the analyte brings both the sensitizer and chemiluminescer particles in close proximity. Activation of sensitizer particles with light results in the formation of singlet oxygen, which is channeled to the particle label reagent.

The foregoing compositions and assays are provided by way of illustration and not limitation to enable one skilled in the art to appreciate the scope of the present invention and to practice the invention without undue experimentation. It will be appreciated that the choice of components, e.g., analytes, label reagents, particles, other reagents and reaction conditions will be suggested to those skilled in the art in view of the disclosure herein and the examples that follow.

The present invention also has application to areas other than assays. For example, the present compositions may be used in photodynamic therapy. A discussion of photodynamic therapy may be found in an article by Levy in *Semin Oncol*, 21(6 Suppl 15):4–10 1994 Dec. Photodynamic therapy (PDT) is based on the use of light-sensitive molecules called photosensitizers. Photoactivation causes the formation of singlet oxygen, which produces peroxidative reactions that can cause cell damage and death. Porfimer sodium (Photofrin, manufactured by Lederle Parenterals, Carolina, Puerto Rico, under license from Quadra Logic Technologies, Inc, Vancouver, BC, Canada) is the photosensitizer that has been studied most extensively. Patients generally have to be hospitalized for 2 days prior to light treatment after administration of porfimer sodium; it takes approximately 48 hours after injection to reach optimal concentration in tumor tissue. The tumoricidal capacity of PDT with porfimer sodium is determined in part by the maximum depth of penetration of light having a wavelength of 630 nm. Porfimer sodium causes cutaneous photosensitivity that may last for up to 6 weeks. Benzoporphyrin derivative (BPD verteporfin; BPD-Quadra Logic Technologies, Inc, Vancouver, BC, Canada), another photosensitizer, accumulates more rapidly in tumor tissue, permitting optimal PDT 30 to 150 minutes following intravenous administration. It is rapidly cleared from the body, and skin photosensitivity does not extend beyond a few days. The primary mechanism of action of PDT is related to the selective accumulation of photosensitizers in cancer tissue. Photodynamic therapy also shows promise in the treatment of a number of non-neoplastic conditions, including psoriasis, macular degeneration of the retina, atherosclerotic plaque and restenosis, bone marrow purging for treatment of leukemias with autologous bone marrow transplantation, inactivation of viruses in blood or blood products, and several autoimmune conditions, including rheumatoid arthritis. Levy also discusses the physiologic characteristics shared by this disparate group of diseases and the mechanisms by which they may mediate photoactivation. Also discussed is a latex nanosphere delivery system (LNDS), which includes nanometer-sized carriers of fluorescent dyes and active agents selectivity target neuronal subpopulations via uptake and retrograde transport.

Madison, et al., *Brain Res*. (1990), 522(1), 90–98 disclose a wide range of latex particles capable of carrying high concentrations of fluorescent dyes, drugs, and photoactive agents selectively to subpopulations of neurons in vitro and in vivo. Bachor, et al., *J Urol*, 146(6):1654–8 1991 Dec disclose free and conjugated chlorin E6 in the photodynamic therapy of human bladder carcinoma cells. The chemistry, photophysics and photosensitizing properties of phthalocyanines is described by van Lier, et al., *Ciba Found Symp*, 146:17–26; discussion 26–32 (1989). Reddi, *J Photochem Photobiol B*, 37(3):189–95 1997 February discusses the role of delivery vehicles for photosensitizers in the photodynamic therapy of tumors. Lipid-based delivery vehicles, such as liposomes and oil emulsions, allow the administration of water-insoluble photosensitizers. Jiang, et al., *J Natl Cancer Inst*, 83(17):1218–25 Sep. 4, 1991 describe the photodynamic killing of human squamous cell carcinoma cells using a monoclonal antibody-photosensitizer conjugate. Yemul, et al., *Proc Natl Acad Sci USA*, 84(1):246–50 1987 January describes selective killing of T lymphocytes by phototoxic liposomes.

The advantageous properties of the compositions of the present invention provide for enhanced and more efficient production of singlet oxygen and, thus, are more effective in delivering the necessary level of singlet oxygen at the site to be treated. More singlet oxygen can be delivered for each particle that binds to diseased tissue and/or less damaging lower laser power can be used. This is due to the ability to introduce higher concentrations of sensitizers into doped particles before the rate of singlet oxygen no longer increases. This higher maximum rate of singlet oxygen formation during irradiation of such particles is able to produce greater tissue damage at sites at which the particles are localized relative to conventional photodynamic therapy sensitizers. Not only does this simplify the laser equipment required for therapy, but more importantly it reduces the amount of damage to peripheral tissue that is in the light path but does not have photosensitizer bound to it. The method is particularly useful when the particles are targeted to the tissue of interest by virtue of some chemical property of their surface such as the attachment of an antibody to an antigen located on the targeted tissue.

Another aspect of the invention is method for determining an analyte, the method comprising (a) combining a sample suspected of containing the analyte with polymeric particles of 20 nm to 100 μm in diameter having dissolved therein (i) 2 to 10% by weight of a dopant and (ii) a photoactive compound and reagents that produce a color change in relation to the amount of the analyte and (b) activating the photoactive compound and relating the intensity of the light emitted to the amount of the color change.

To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as enzyme substrates, additional sbp members, ancillary reagents and so forth. The relative amounts of the various reagents in the kits can be varied widely to provide for concentrations of the reagents that substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (° C.).

Melting points were determined on a Hoover capillary apparatus and are uncorrected. 'HNMR spectra were recorded on a Brucker WP-250 MHz or Brucker WP-300 MHz NMR spectrometer. Chemical shifts were reported in parts per million (0.0). NMR multiplicities are recorded by use of the following abbreviations: s, singlet; d, doublet; t, triplet; m, multiplet; Hz, hertz. Infrared spectra were recorded on a Perkin-Elmer 2971R spectrometer. Desorption chemical ionization (C.I.) and electron ionization (E.I.) were done on a Varian-MAT 311A, double focusing high-resolution mass spectrometer. A Finnigan TSQ-70 or MAT-8230 was used for fast atom bombardment mass spectra (FAB/LSIMS). UV-visible absorption spectra were done on a HP 8452A diode array spectrophotometer. Fluorescence and chemiluminescence measurements were done on a Spex fluorolog spectrophotometer or a Perkin Elmer 650-40 spectrophotometer. Chemiluminescence measurements were also performed on an in-house chemiluminometer (Oriel box).

Toluene was distilled from sodium over argon. Unless mentioned otherwise, all solvents were used without purification, and most reactions were carried out under argon. Silica gel used for flash chromatography was 230–400 mesh ASTM, purchased from Scientific Products while preparative plates (10000 ( )) and analytical plates were purchased from Analtech.

C-28 thioxene, substituted N-phenyl oxazine and thioxene attached to 9,10-bis(phenylethynyl) anthracene (BPEA) were prepared as described below. 2-Chloro 9,10-bis(phenylethynyl) anthracene (1-Cl-BPEA) and rubrene (5,6,11,12-tetraphenyl naphthacene) were purchased from Aldrich Chemical Co. Rubrene was recrystallized from methylene chloride and stored at 4° C. in a brown bottle prior to use. Silicon phthalocyanine was prepared as described below and phthalocyanine tetrasulfonates was obtained from Ultra Diagnostics, Inc. Carboxylate-modified polystyrene (latex) particles were purchased from Seradyn, Inc. The particles were 203 nm. The carboxyl parking area was 49.5 angstroms squared (0.09 milliequivalents/g). Solids were 10% (100 mg/ml). 2-ethoxyethanol was from Aldrich Chemical Co. and was redistilled under vacuum. Sodium hydroxide was 0.1 N. Isopropanol was from Aldrich Chemical Co.

Unless otherwise indicated, oligonucleotides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10× solution) from BioWhittaker, Walkersville, Md.

DTT—dithiothreitol from Sigma Chemical Company, St. Louis, Mo.

HPLC—high performance liquid chromatography.

DPP—4,7-diphenylphenanthroline from Aldrich Chemical Company, Milwaukee Wis.

BSA—bovine serum albumin from Sigma Chemical Company, St. Louis Mo.

ELISA—enzyme linked immunosorbent assay as described in "Enzyme-Immunoassay," Edward T. Maggio, CRC Press, Inc., Boca Raton, Fla. (1980)

bp—base pairs
ddc—dideoxycytidine
g—grams
mmol—millimoles
mM—millimolar
pM—picomolar
DMF—dimethyl formamide
THF—tetrahydrofuran
LSIMS—fast ion bombardment mass spectroscopy
NMR—nuclear magnetic resonance spectroscopy
TMSCl—tetramethylsilylchloride
EDAC—1-ethyl-3-(3-dimethylaminopropyl)-carbodiimide hydrochloride.
MES—2-(N-morpholino)ethane sulfonic acid.
SPDP—N-succinimidyl 3-(2-pyridylthio)-propionate.
Sulfo-SMCC—N-sulfosuccinimidyl-4-(N-maleimidomethyl)cyclohexane-1-carboxylate.
TCEP—tris-carboxyethyl phosphine.
SATA—N-succinimidyl S-acetylthioacetate
TSH—thyroid stimulating hormone
HbsAg—hepatitis B surface antigen
RLU—relative light units Preparation of Reagents N-phenyl oxazine (NPhe):

The N-phenyl oxazine was prepared by a procedure similar to that described in U.S. Pat. No. 5,578,498 (Singh, et al.) for the preparation of compound 16. The relevant disclosure of the above patent is incorporated herein by reference.

C-28 thioxene:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90(C for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3 times). The combined organic phases were washed with $H_2O$ (2×), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate: hexane) afforded 24.7 g (50%) of the benzoin product (LSIMS ($C_{42}H_{69}NO_2$): [M–H]$^+$ 618.6, $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (LSIMS ($C_{44}H_{71}NOS$): [M–H]$^+$ 661.6, $^1$H NMR (250 MHz, $CDCl_3$) was consistent with the expected C-28 thioxene product 2-(4-(N,N-di-($C_{14}H_{29}$)-anilino)-3-phenyl thioxene.

Silicon tetra-t-butyl phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCl Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (LSIMS: $[M–H]^+$ 1364.2, absorption spectra: methanol: 674 nm ((180,000): toluene 678 nm, $^1H$ NMR (250 MHz, $CDCl_3$): (: –2.4(m, 12H), –1.3(m, 12H), 0.2–0.9 (m, 54H) 1.8(s, 36H), 8.3(d, 4H) and 9.6 (m, 8H) was consistent with the above expected product.

Hydroxypropylaminodextran (1$NH_2$/7 glucose) was prepared by dissolving Dextran T-500 (Pharmacia, Uppsala, Sweden) (50 g) in 150 mL of $H_2O$ in a 3-neck round-bottom flask equipped with mechanical stirrer and dropping funnel. To the above solution was added 18.8 g of Zn $(BF_4)_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran (1$NH_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

Sensitizer Particles Having Silicon tetra-t-butyl Phthalocyanine Incorporated Therein and Having Streptavidin Immobilized on their Surface:

Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 40 mg of silicon tetra-t-butyl phthalocyanine prepared as described above was added; the beads were stirred for 5 minutes more. At this point 1.0 mL of 0.1 N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of 10% aqueous ethanol to a final volume of 40 mL.

Streptavidin was bound to the above beads using 25 mg streptavidin for 100 mg of beads. 25 mg streptavidin (50 mg Aaston solid from Aaston, Wellesley, Mass.) was dissolved in 1 mL of 1 mM EDTA, pH 7.5, and 77 µL of 2.5 mg/mL SATA in ethanol was added thereto. The mixture was incubated for 30 min at room temperature. A deacetylation solution was prepared containing 1M hydroxylamine-HCl, 50 mM $Na_2PO_4$, 25 mM EDTA, pH 7.0. 0.1 mL of this deacetylation solution was added to the above solution and incubated for 1 hr at room temperature. The resulting thiolated streptavidin was purified on a Pharmacia PD10 column and washed with a column buffer containing 50 mM MOPS, 50 mM EDTA, pH 7.2. The volume of the sample was brought to 2.5 mL by adding 1.5 mL of the above column buffer. The sample was loaded on the column and eluted with 3.5 mL of the column buffer. The thiolated streptavidin was diluted to 5 mL by adding 1.5 mL of 50 mM MOPS, 50 mM EDTA, 0.1% Tween-20, pH 7.2. 5 mL of the thiolated streptavidin solution was added to 5 mL of maleimidated sensitizer beads prepared as described above, under argon, and mixed well. The beads were topped with argon for 1 min, the tube was sealed and the reaction mixture was incubated overnight at room temperature in the dark.

To the above beads was added 7.5 mL of 50 mM MOPS, 50 mM EDTA, 0.1% Tween-20, pH 7.2 to bring the beads to 1 mg/mL. The remaining maleimides were capped by adding mercaptoacetic acid at a final concentration of 2 mM. The mixture was incubated in the dark for 30 min at room temperature. The remaining thiols were capped by adding iodoacetic acid at a final concentration of 10 mM and the mixture was incubated at room temperature for 30 min in the dark. The beads were centrifuged for 30 min at 15,000 rpm (Sorvall RC-5B) as above for a total of three times.

Preparation of TAR Particles

Microgon setup: A Microgon was assembled as described in the "Minikros Lab Systems" manual, pages 8–10. A 0.1 micron module was used operated between about 5–10 psi. The Microgon apparatus was washed with ethanol (200 proof).

Setup of Apparatus:
1. An oil bath was heated to 95° C.±3° C. A three-necked 1 liter roundbottom flask (rbf) equipped with a digital cafeama mechanical stirrer from the middle neck was immersed into the oil bath.
2. Addition of particles: 200 ml±5.0 ml of latex particles were added to the rbf by means of a measuring cylinder, which was washed with 2×30 ml of ethoxyethanol (ee) and the contents were transferred to the rbf. To the flask was added 20±5 ml of 0.1 N sodium hydroxide. The particles were stirred at 330 rpm per minute at 95° C. for 20 minutes.
3. Addition of C-28 thioxene: 3.6 grams of C-28 thioxene was dissolved in 85 ml of ethoxyethanol and the resulting solution was added to the particles dropwise over 85–100 minutes at a constant addition rate of approximately 1.0 ml per minute. The particles were stirred for 5 minutes and 6.0 ml of 0.1 N sodium hydroxide and 30 ml of deionized water were added over 10 minutes. The particles were stirred for 5 minutes.
4. Addition of 1-Cl-BPEA): 1 gram of 1-Cl-BPEA was added to 155 ml of ee and gently heated at 95° C. to dissolve the 1-Cl-BPEA. The ethoxyethanol solution of 1-Cl-BPEA was added to the particles over 60–70 minutes. The particles were stirred for 5 minutes and 6.0 ml of 0.1 N sodium hydroxide and 12 ml of deionized water were added to the particles over 5 minutes. The particles were stirred for 10 minutes.
5. Addition of Rubrene: rubrene (recrystallized M.P. 328° C.–329° C., 480 mg) was dissolved in 200 ml of 1,2-dimethoxyethane and was then added with stirring to the above particles over 70–90 minutes. Rate of addition was 3.0 ml per minute. Next, 30 ml of 0.1 N sodium hydroxide and 120 ml of deionized water were added to the particles over 30 minutes and the medium was stirred for 10 minutes. The medium was cooled to 40° C. over 1 hour with stirring. The particles were subjected to filtration on a Microgon apparatus using a 43 micron (Tetko) filter (from Tetko Inc., Briarcliff Manor, N.Y.).

The particles were determined to have approximately 15% by weight of dyes incorporated therein and the concentration of the particles was 37 mg/ml. The size of the particles was 216 nm±17 nm. The concentration of dyes was as follows: C-28 thioxene, approximately 100 mM; 1-Cl-BPEA, approximately 43 mM; and rubrene, approximately 21.5 mM.

Preparation of N-Phe Particle

Microgon setup: A Microgon was assembled as described in the Minikros lab system manual page 8–10. A 0.1 micron module was used operated between about 5–10 psi. The Microgon apparatus was with ethanol (200 proof).

Setup of Apparatus:
1. An oil bath was heated to 95° C.±1.0° C. A three-necked 1 liter roundbottom flask (rbf) equipped with a digital Cafeama mechanical stirrer from the middle neck was immersed into the oil bath.
2. Addition of particles: 200 ml±5.0 ml of latex particles were added to the rbf by means of a measuring cylinder, which was washed with 2×30 ml of ethoxyethanol (ee) and the contents were transferred to the rbf. To the flask was added 20±5 ml of 0.1 N sodium hydroxide. The particles were stirred at 330 rpm at 95° C. for 20 minutes.
3. Addition of N-Phe: N-Phe (1.93 gram, 5.4 mmol) was dissolved in 85 ml of ethoxyethanol and the resulting solution was added to the particles dropwise over 85–100 minutes at a constant addition rate of approximately 1.0 ml per minute. The particles were stirred for 5 minutes, and 6.0 ml of 0.1 N sodium hydroxide and 30 ml of deionized water were added over 10 minutes. The particles were stirred for 5 minutes.
4. Addition of Rubrene: Rubrene (480 mg, 0.9 mmol) was dissolved in 200 ml of 1,2-dimethoxyethane and was then added with stirring to the above particles over 70–90 minutes. Rate of addition was 3.0 ml per minute. Next, 30 ml of 0.1 N sodium hydroxide and 120 ml of 0.1 N sodium hydroxide and 120 ml of deionized water were added to the particles over 30 minutes and the medium was stirred for 10 minutes. The medium was cooled to 40° C. over 1 hour with stirring. The particles were subjected to filtration on Microgon apparatus using a 43 micron (Tetko) filter (from Tetko Inc. Briarcliff Manor, N.Y.).

Example 1

Preparation of Plasticized Photoactive (DopTAR) Particles

Microgon Setup:

A Microgon was assembled as described in the 'Minikros lab systems' manual, pages 8–10. A 0.1 micron module was used operated between about 5–10 psi. The Microgon apparatus was washed with ethanol (200 proof).

Materials:
1. TAR particles prepared as described above.
2. N-Heptadecylbenzene from Pfaltz & Bauer
3. Ethanol
4. Aminodextran (one amine per 15.5 glucoses)
5. EDAC (Sigma)
6. Dextran aldehyde (8–9 aldehydes per sugar)
7. Sodium Cyanoborohydride
8. MES buffer
9. Sodium Chloride Procedure:
1. The reaction was performed in a 500 ml conical flask, which is capped and covered with aluminum foil. To the conical flask were added 0.5 ml of N-heptadecylbenzene (as dopant) and 10 ml of ethanol. Aminodextran (1.0 g) was dissolved in 20 ml of 50 mM MES buffer (pH=6.0) (50 mg/mL) and then added to the conical flask. Next, 30 mL of MES buffer (50 mM, pH=6.0) was added to the conical flask, which was then shaken or vortexed. Eighty (80) mL of the medium containing the photoactive TAR particles (25 mg/mL) was added to the conical flask, which was again shaken or vortexed. To the flask was added 60 mL of MES buffer (50 mM, pH a 6.0). The flask was covered with aluminum foil and placed in a shaker at 80–85° C.

After approximately 16 hours in the shaker, the temperature of the particles is allowed to decrease to room temperature. EDAC (400 mg) was dissolved in 5.0 mL of deionized water and added to the above flask one mL at a time with shaking over ten minutes. The flask was returned to the shaker for 16 hours at room temperature. An equal volume of 1.0 M NaCl in the MES buffer was added to the conical flask. The mixture was charged on a Microgon set up and the particles were concentrated to 25 to 50 ml. The particles were washed with one to two liters of 0.5 M NaCl in the MES buffer. The size of the particles was determined using a NICOMP instrument.

The concentrations of dye were thioxene 100 mM; Cl-BPEA-25 mM and Rubrene 35 mM; the plasticizer was present at a level of 20% by weight. The dextran concentration on the beads was determined to be 10±2% by the well-known anthrone method. Two (2) g of the amino-coated particles were resuspended at 20 mg/mL in MES buffer (pH=6.0, 50 mM and 0.5 M NaCl). The total volume was 100 mL.

Aliquots (10 mL) of the above suspension were taken and sonicated for 50 pulses. The sonicated bead suspension was added dropwise to 240 ml of pre-filtered dextran aldehyde (60 mg/mL) in a 500 ml bottle with shaking. Twelve (12) mL of a freshly prepared solution of 40 mg/mL of $NaCNBH_3$ were added to the beads, which were incubated at 37° C. for 48 hours on a shaker. The particles were then subjected to the Microgon apparatus.

Example 2

Chemiluminescence Decay of Doped Particles

Figure 2:
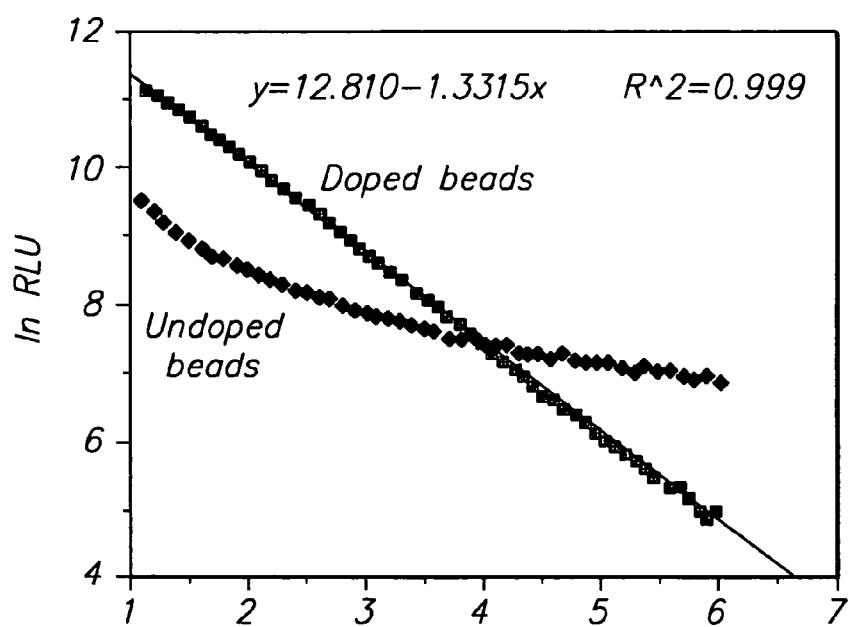
FIG. 2 is a log plot of the graph of FIG. 1.

Fifty (50) μg of chemiluminescer particles (doped with heptadecylbenzene or undoped) and 50 nM phthalocyanine tetrasulphonic acid were mixed in 1.0 ml of Tris buffer (pH 8.0; 50 mM). All measurements in this example and those set forth below were carried out using a manual reader built in-house. This reader was similar to conventional readers except that it had a mechanism for fast filter change. The reader illuminates the sample with a 675 nm laser, then reads emitted light with a photomultiplier tube using appropriate shutters and filters. The solution was placed in the reader (temperature 37° C.) and was irradiated at 680 nm for 1 sec and after a 50-millisecond delay chemiluminescence a reading was recorded for six sec. A plot of signal intensity versus time for both doped and undoped particles is shown in FIG. 1. A log plot is shown in FIG. 2. For beads doped in accordance with the present invention, the chemiluminescence decay was monophasic with a half-life of 0.52 sec at 37° C. For undoped beads the chemiluminescence decay was multiphasic.

Example 3

Stability of Doped Particles

Figure 3:
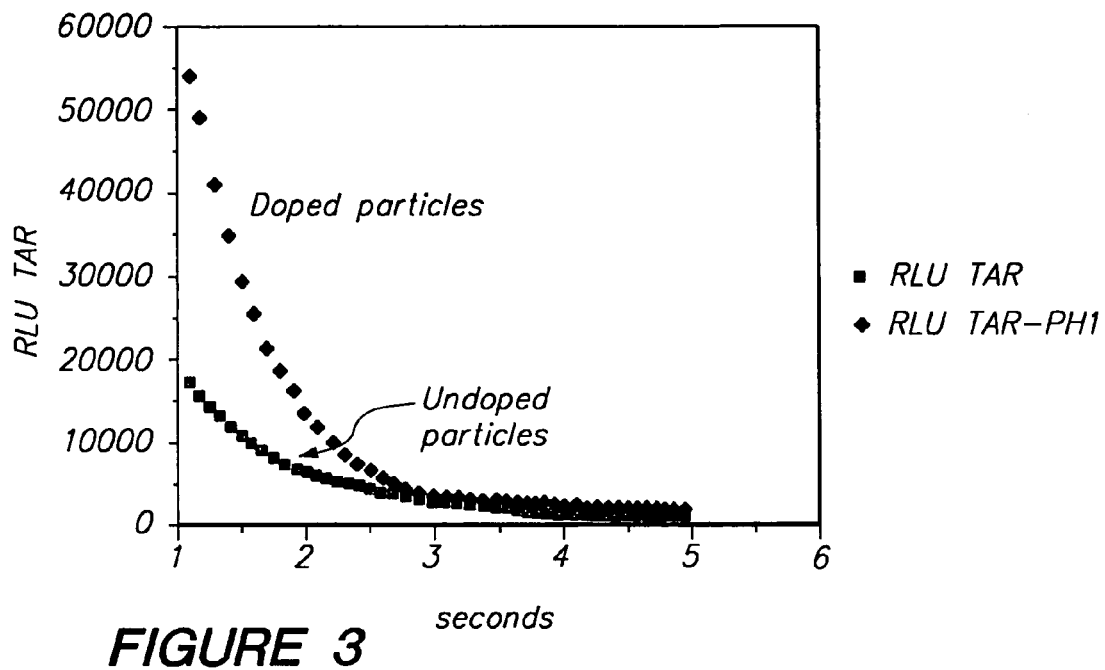
FIG. 3 is a graph showing a plot of signal intensity versus time for particles in accordance with another embodiment of the present invention and particles of the prior art.
Figure 4:
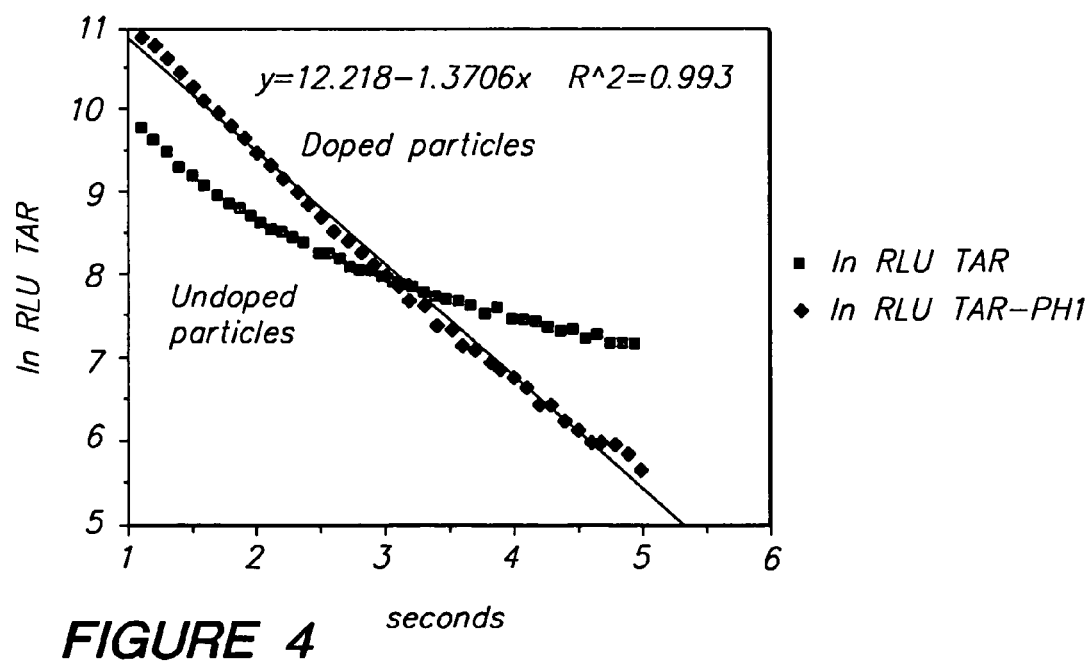
FIG. 4 is a log plot of the graph of FIG. 3.

Fifty (50) μg of antibody (TSH)-coated chemiluminescer particles (doped with heptadecylbenzene or undoped) were prepared in a manner similar to that described in U.S. Pat. No. 5,618,732, the relevant disclosure of which is incorporated herein by reference. These particles were added to 1.0 ml of Tris buffer (pH 8.0; 50 mM with 1% Zwittergen (Sigma Chemical Company) and incubated at 37° C. for 3 days. 50 nM phthalocyanine tetrasulphonic acid was added to the incubated solutions of particles. The solution was placed in the reader instrument (temperature 37° C.). The solution was irradiated at 680 nm for 1 sec and after a 50-millisecond delay chemiluminescence a reading was recorded for five sec. A plot of signal intensity versus time for both doped and undoped particles is shown in FIG. 3. A log plot is shown in FIG. 4. For beads doped in accordance with the present invention, the chemiluminescence decay was monophasic and the half-life was 0.50 sec at 37° C.

Example 4

Thermal Stability of Doped Particles

Figure 5:
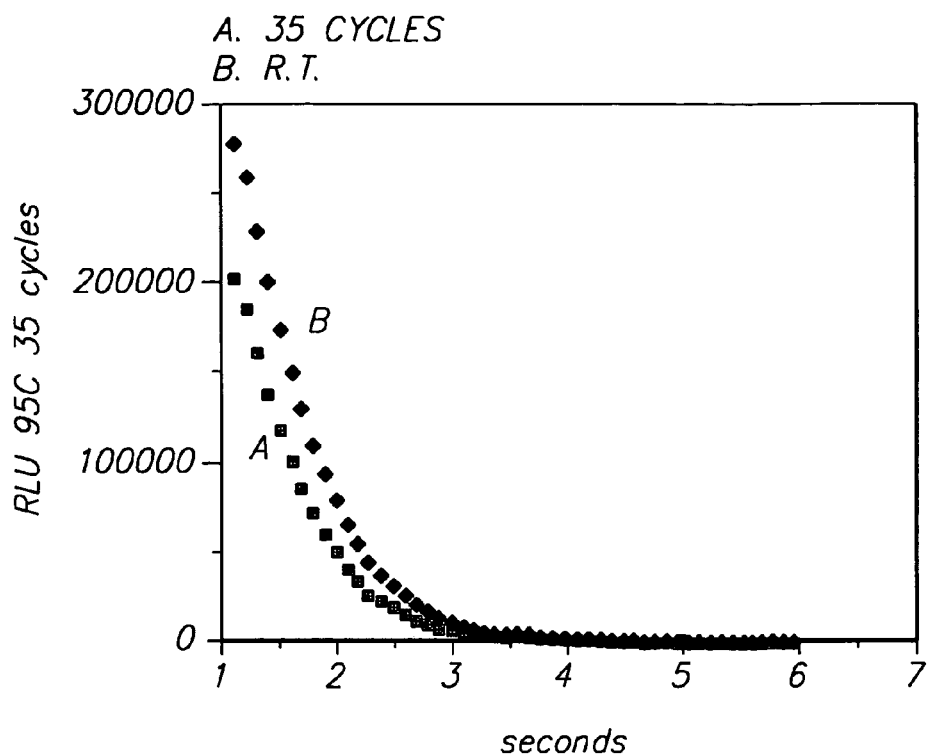
FIG. 5 is a graph showing a plot of signal intensity versus time in a thermal stability study for particles in accordance with the present invention and particles of the prior art.
Figure 6:
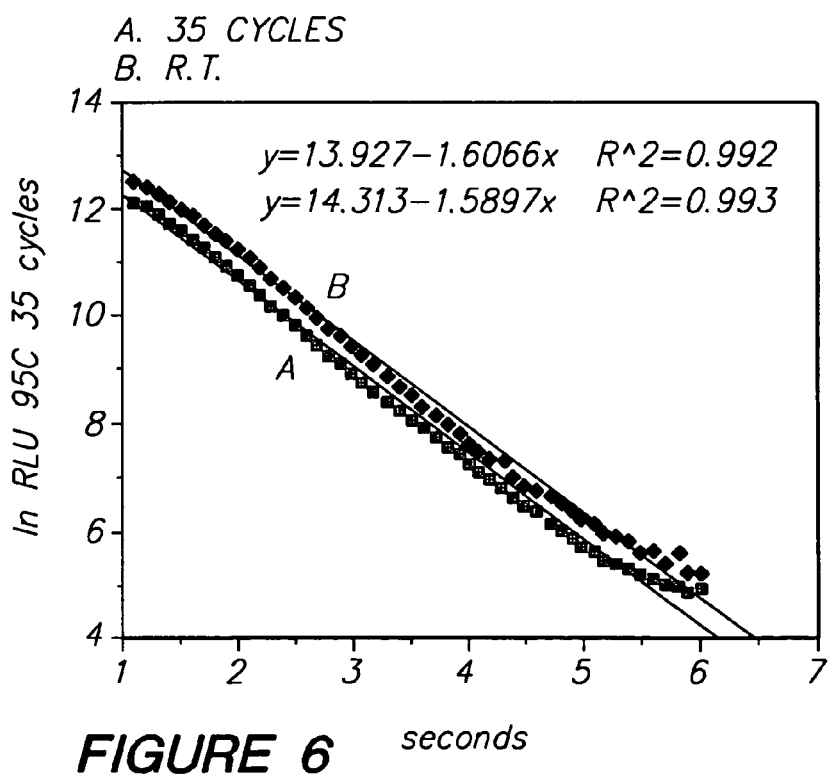
FIG. 6 is a log plot of the graph of FIG. 5.

Fifty (50) μg of dextran aldehyde-coated chemiluminescer particles (heptadecyl benzene doped) and 200 μg of hydrazine-coated sensitizer beads were added to 1.0 ml of Tris buffer (pH 8.0; 50 mM) and incubated at 37° C. for 18 h. The hydrazine coating was carried out by a procedure well-known in the art. 100 μL of incubated solution was added to 0.9 mL Buffer B (10 mM TRIS buffer, pH 8.3, 50 mM KCl, 4 mM $MgCl2$ and 0.2 mg/ml acetylated BSA). One set of tubes was thermocycled for 35 cycles. (Each cycle=96° C. for 60 sec; 74° C. for 30 sec and 65° C. for 60 sec). The solution was placed in the aforementioned reader instrument (temperature 40° C.). The solution was irradiated at 680 nm for 1 sec and after a 50-millisecond delay chemiluminescence was recorded for six sec. A plot of signal intensity versus time for both doped and undoped particles is shown in FIG. 5. A log plot is shown in FIG. 6.

Example 5

Stability of Perfluorodecalin Doped Particles

Figure 7:
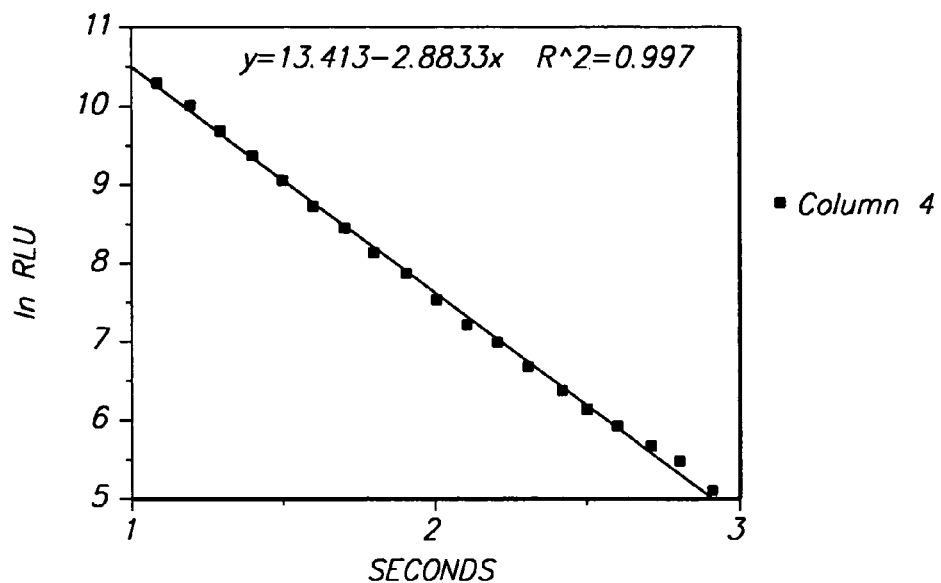
FIG. 7 is a graph showing a plot of signal intensity versus time for particles in accordance with another embodiment of the present invention.

Fifty (50) μg of antibody (TSH)-coated chemiluminescer particles (doped with perfluorodecalin) were added to 1.0 ml of Tris buffer (pH 8.0; 50 mM with 0.1% Tween-20) and incubated at 37° C. for 2 days. The perfluorodecalin particles were prepared in a manner similar to that for the particles containing heptadecyl benzene. 50 nM phthalocyanine tetrasulphonic acid was added to the incubated solutions of particles. The solution was placed in aforementioned reader instrument (temperature 37° C.). The solution was irradiated at 680 nm for 1 sec and after a 50-millisecond delay chemiluminescence was recorded for five sec. A plot of natural log of signal intensity versus time for particles doped with perfluorodecalin is shown in FIG. 7. The chemiluminescence decay was monophasic and the half-life was 0.24 seconds at 37° C. As shown above, the half-life of beads doped with heptadecylbenzene was 0.52 sec under the same conditions.

Example 6

Chemiluminescence Decay at Two Different Temperatures

Figure 8:
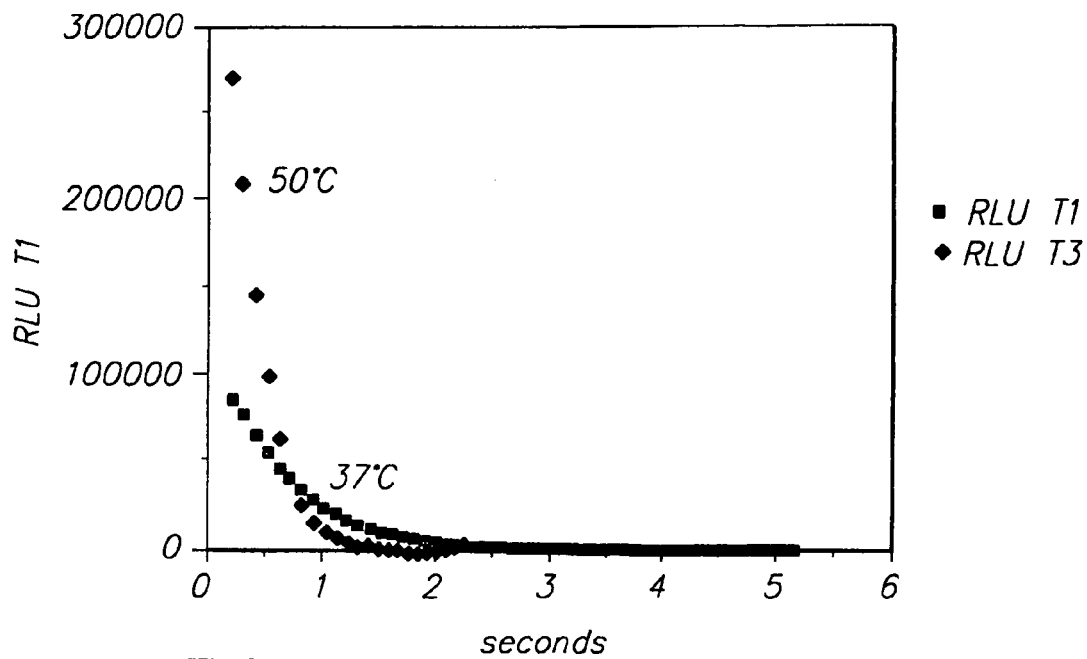
FIG. 8 is a graph showing a plot of signal intensity versus time in a study of chemiluminescent decay at two different temperatures for particles in accordance with the present invention and particles of the prior art.
Figure 9:
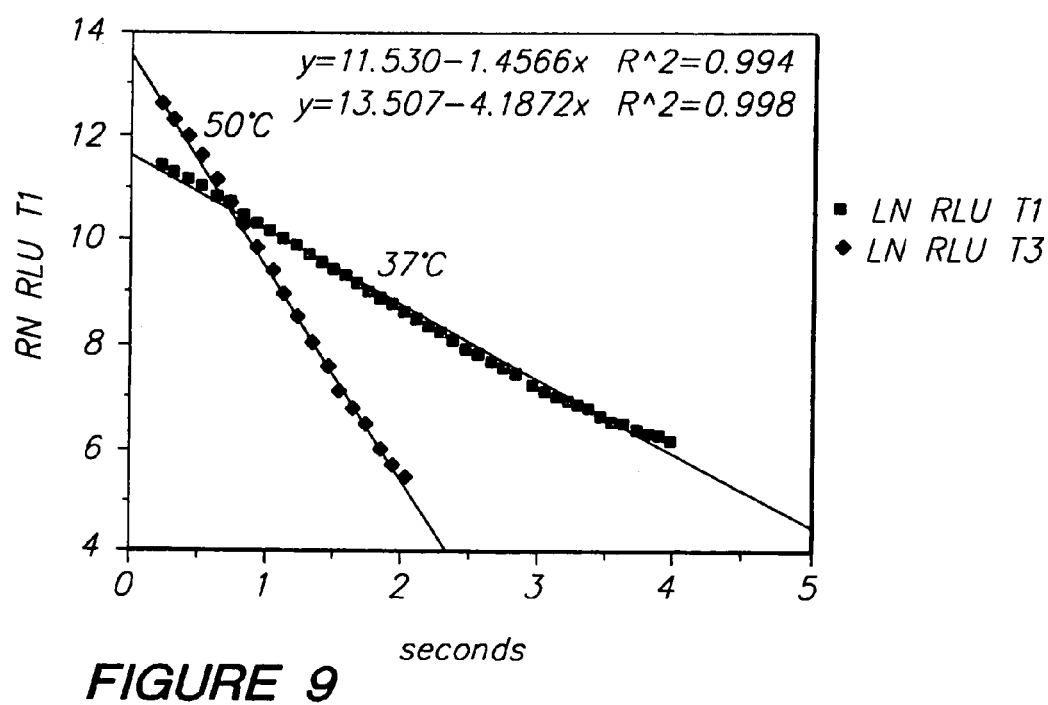
FIG. 9 is a log plot of the graph of FIG. 8.

Fifty (50) μg of chemiluminescer particles (doped with heptadecyl benzene or undoped) and 50 nM phthalocyanine tetrasulphonic acid ware mixed in 1.0 ml of Tris buffer (pH 8.0; 50 mM). The solution was placed in the aforementioned reader instrument (temperature 37° C. or 50° C.). The solution was irradiated at 680 nm for 1 sec and after a 50-millisecond delay chemiluminescence was recorded for four seconds. A plot of signal intensity versus time for both doped and undoped particles is shown in FIG. 8. A log plot is shown in FIG. 9. The chemiluminescence decay was monophasic for doped beads and the half-life was 0.48±0.05 sec at 37° C. and 0.166 sec at 50° C.

Example 7

HbsAg Assay Using Doped Chemiluminescer Beads

Figure 10:
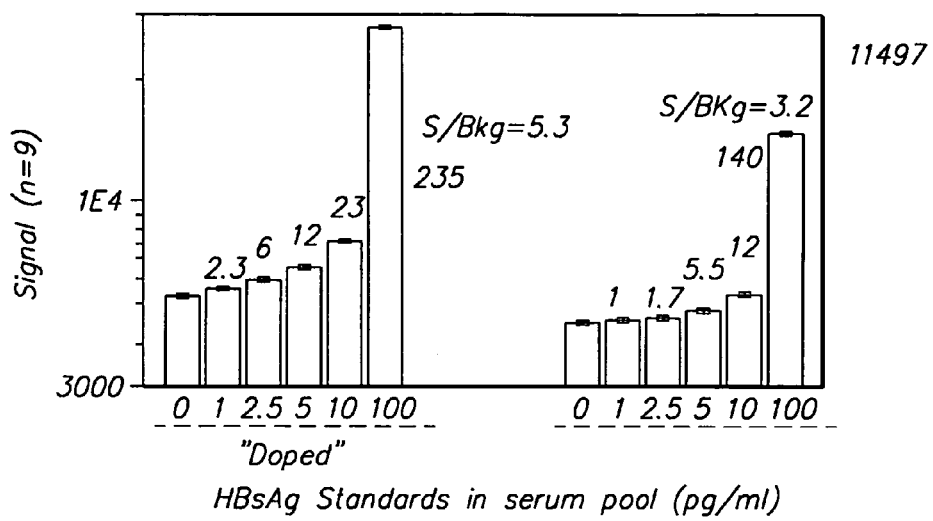
FIG. 10 is a graph depicting the results of an assay for HbsAg using particles in accordance with the present invention and particles of the prior art.
Figure 11:
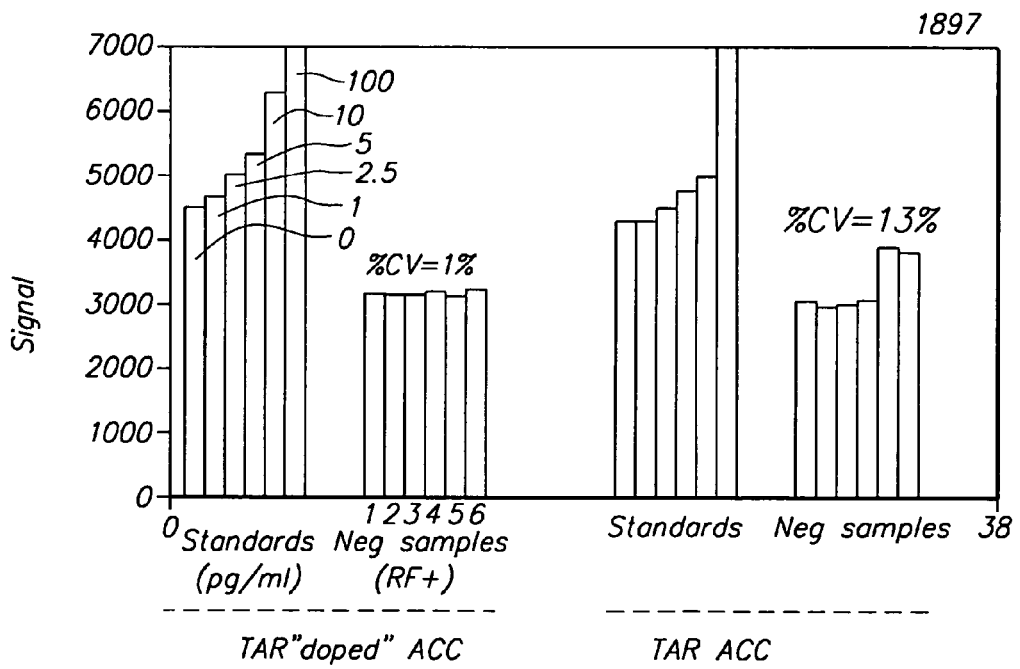
FIG. 11 is a graph depicting results from a comparison of particles in accordance with the present invention and particles of the prior art on six problematic samples from the assay to which FIG. 10 pertains.

HbsAg standards in pooled serum (0 to 100 pg/mL) were added to either anti-HbsAg antibody coated doped and undoped chemiluminescer beads (2 µg per assay) and biotinylated antibody-2 in 0.8 mL of Buffer B and incubated for 20 min. 20 µg of streptavidin beads in 0.2 mL of Buffer B was added to the assay mixture and incubated for 10 min. Signal was recorded by irradiating the sample with 680 nm light for 1 sec and after 50 milliseconds emitted light was collected for one sec (550–650 nm bandpass filter). The procedure was repeated six times and total signal was plotted in FIG. 10. CV was determined for 1500 negative samples from a blood bank for both doped and undoped beads. The CV for both sets of beads for 1500 samples was between 2–3%. Six problematic samples for doped and undoped beads are compared on in FIG. 11.

Example 8

HbsAg Assay Using Doped Sensitizer Beads

HbsAg standards in pooled serum (0 to 100 pg/mL) ware added to either anti-HbsAg antibody coated undoped chemiluminescer beads (2 µg per assay) and biotinylated antibody-2 in 0.8 mL of Buffer B and incubated for 20 min. 20 µg of doped and undoped streptavidin beads in 0.2 mL of Buffer B was added to the assay mixture and incubated for 10 min. Signal was recorded by irradiating the sample with 680 nm light for 1 sec and after 50 milliseconds emitted light was collected for one sec (550–650 nm bandpass filter). The procedure was repeated for six cycles and total signal (average of three experiments) is tabulated below in Table 1.

TABLE 1

|  | pg/ml | Signal |
|---|---|---|
| Doped beads | 0 | 3199 |
|  | 10 | 4422 |
|  | 50 | 10091 |
|  | 100 | 16526 |
| Undoped beads | 0 | 2464 |
|  | 10 | 3446 |
|  | 50 | 6832 |
|  | 100 | 11114 |

Example 9

TSH Assay Using Doped Chemiluminescer Beads

Figure 12:
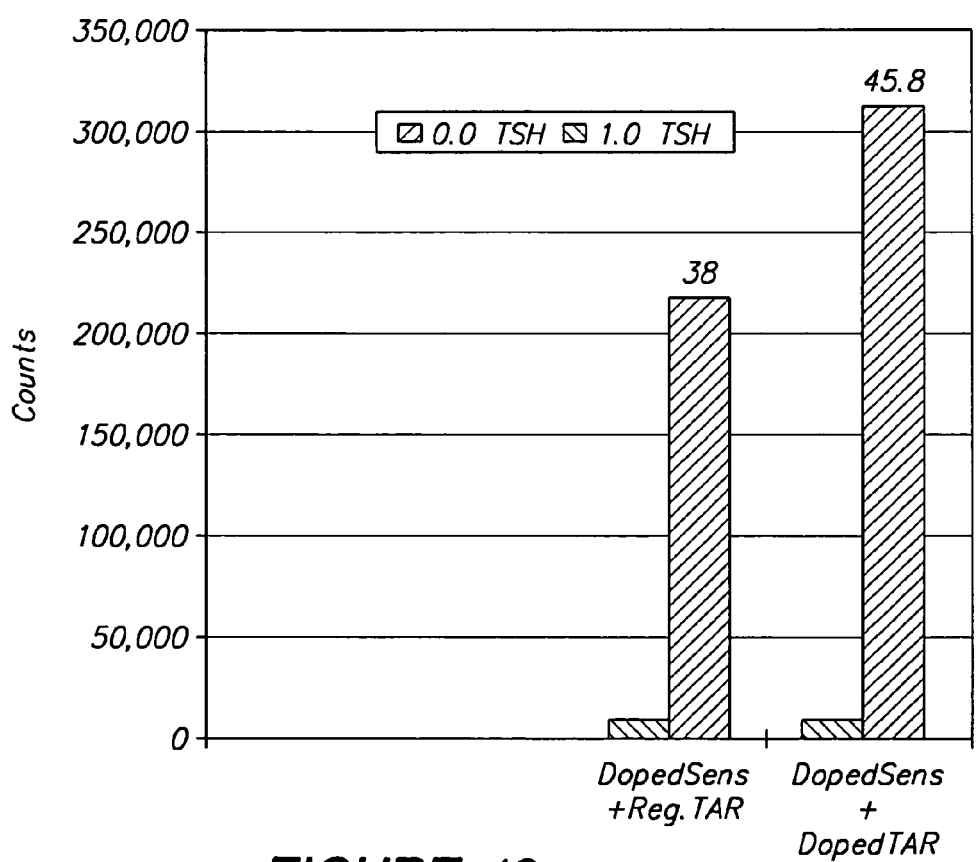
FIG. 12 is a graph depicting the results of an assay for TSH using particles in accordance with the present invention and particles of the prior art.

TSH standards in pooled serum (0 and 1 µIU/mL) were added to either anti-TSH antibody-coated doped and undoped chemiluminescer beads (2 µg per assay) and biotinylated antibody-2 in 0.8 mL of Buffer B and incubated for 20 min. 20 µg of streptavidin beads in 0.2 mL of Buffer B was added to the assay mixture and incubated for 10 min. Signal was recorded by irradiating the sample with 680 nm light for 1 sec and after 50 milliseconds emitted light was collected for one sec (550–650 nm bandpass filter). The procedure was repeated six times and total signal is tabulated below in Table 2 and plotted in FIG. 12.

TABLE 2

|  | 0.0 µIU/ml TSH | 1.0 µIU/ml TSH | S/So* |
|---|---|---|---|
| Doped beads | 6474 | 365,638 | 57 |
| Undoped beads | 5884 | 160,832 | 28 |

*Signal/Background

Example 10

TSH Assay Using Doped Sensitizer Beads

TSH standards in pooled serum (0 and 1.0 µU/mL) were added to either anti-TSH antibody-coated undoped chemiluminescer beads (2 µg per assay) and biotinylated antibody-2 in 0.8 mL of Buffer B and incubated for 20 min. 20 µg of doped and undoped streptavidin beads in 0.2 mL of Buffer B was added to the assay mixture and incubated for 10 min. Signal was recorded by irradiating the sample with 680 nm light for 1 sec and after 50 milliseconds emitted light was collected for one sec (550–650 nm bandpass filter). The procedure was repeated for six cycles and total signal (average of three experiments) is tabulated below in Table 3.

TABLE 3

|  | µIU/ml | Signal |
|---|---|---|
| Doped beads | 0 | 5686 |
|  | 1 | 216229 |
| Undoped beads | 0 | 3204 |
|  | 1 | 71874 |

Example 11

Homogenous Qualitative Detection of Wild-Type HIV and Internal Control (ELGA)

Preparation of Oligonucleotide-Bound Particles:

Oligonucleotide was immobilized on the surface of particles for use in the experiments herein in the following manner. Aminodextran (500 mg) was partially maleimidated by reacting it with sulfo-SMCC (157 mg, 10 mL $H_2O$). The sulfo-SMCC was added to a solution of the aminodextran (in 40 mL, 0.05 M $Na_2HPO_4$, pH 7.5) and the resulting mixture was incubated for 1.5 hr. The reaction mixture was then dialyzed against MES/NaCl (2×2 L, 10 mM MES, 10 mM NaCl, pH 6.0, 4° C.). The maleimidated dextran was centrifuged at 15,000 rpm for 15 minutes and the supernatant collected. The supernatant dextran solution (54 mL) was then treated with imidazole (7 mL of 1.0 M solution) in MES buffer (pH 6.0) and into this stirred solution was added the stained particles (photosensitizer or chemiluminescer) (10 mL of 10 mg/mL). After stirring for 10 minutes the suspension was treated with EDAC (7 mmol in 10 mM pH 6.0 MES) and the suspension stirred for 30 minutes. After this time, SurfactAmps® (Pierce Chemical Company) Tween-20 (10%, 0.780 mL) was added to the reaction mixture for a final concentration of 0.1%. The particles were then centrifuged at 15,000 rpm for 45 minutes and the supernatant discarded. The pellet was resuspended in MES/NaCl (pH 6.0, 10 mM, 100 mL) by sonication. Centrifugation at 15,000 rpm for 45 minutes, followed by pellet resuspension after discarding the supernatant, was performed twice. The maleimidated dextran particles were stored in water as a 10 mg/mL suspension.

Thiolated oligonucleotide (oligonucleotide bearing a 5'-bis(6-hydroxyethyldisulfide) group) (Oligos Etc.) was dissolved in water at a concentration of 0.49 mM. To 116 µL of this solution was added 8.3 µL of 3.5 M sodium acetate, pH 5.3 and 8.9 µL of tris(carboxyethyl)phosphine (20 mM). After 30 minutes incubation at room temperature, 548 µL of cold ethanol was added and the mixture was maintained at about −20° C. for 1.5 hour. The precipitated oligonucleotide was recovered by centrifugation for 2 min. at 15,000 rpm in an Eppendorf centrifuge, then dissolved in 37.5 µL of 5 mM sodium phosphate, 2 mM EDTA, pH 6.

An aliquot of the maleimidated beads prepared above containing 22 mg beads was centrifuged for 30 min. at about 37,000 g, and the pellet was resuspended in 96 µL of 0.26 M NaCl, 0.05% Tween-20, 95 mM sodium phosphate, and 0.95 mM EDTA, pH7. The thiolated oligonucleotide was added and the mixture was maintained at 37° C. for 64 hours under argon. A 10 µL aliquot of sodium thioglycolate was added and incubation was continued for 2 hours at 37° C. Water was added to a total volume of 1 mL, and the beads were recovered by centrifugation, then resuspended in 5 mL of 0.1 M NaCl, 0.17 M glycine, 10 mg/mL BSA, 1 mM EDTA, 0.1% Tween-20, and 0.5 mg/mL Calf thymus DNA (Sigma Molecular Biology grade), pH 9.2. After three hours, the beads were recovered and washed three times by centrifugation, twice in buffer A and once in standard PCR buffer. The product was stored refrigerated in PCR buffer. Buffer A contained 0.1 M Tris base (J. T. Baker Chemical Co.), 0.3 M NaCl (Mallinckrodt), 25 mM EDTA $Na_2H_2O$ (Sigma Chemical Co.), 0.1% BSA (Sigma Chemical Co.), 0.1% dextran T-500 (Pharmacia), HBR-1 (Scantibodies), 0.05% Kathon and 0.01% gentamicin sulfate (GIBCO) prepared by dissolving and adjusting pH to 8.20 with concentrated HCl and made up to 10 L with distilled water.

The above procedure may be modified in a manner similar to that described by Ullman, et al., Proc. Natl. Acad. Sci. USA (1994) 91:5426–5427 at column 1 of page 5427.

Detection of Wild-Type HIV and Internal Control (ELGA)

Target HIV RNA (obtained from Organon Teknika, Boxtel, Netherlands) was amplified by the isothermal NASBA amplification procedure. The NASBA Amplification Kit of Organon Teknika was employed. A probe specific for Wild-Type (WT) was attached to dopTAR beads. A probe specific for Internal Control (ELGA) was attached to N-phenyl oxazine beads (chemiluminescer beads with 30 sec decay half-life). Sensitizer beads had attached thereto probes that recognize both WT and ELGA sequence. NASBA amplification was performed as described in U.S. Pat. No. 5,130,238, the relevant disclosure of which is incorporated herein by reference. The amplification was carried out in the presence of 62.5 nM probe (4 different probes) and 1.25 µg of each type of bead (2 chemiluminescer and two sensitizers). The 20 µL reaction was incubated for 90 min at 41° C. The signal was read and is tabulated below in Table 4. Read Cycle: 0.1 sec irradiation, 0.5 sec read; 30 sec delay and 5 sec read.

From raw signal the 5 sec window exhibited chemiluminescence from n-Phenyl Oxazine beads only. This could only occur when doped TAR beads were used since the decay is monophasic. When undoped TAR beads were used, the signal spills over into the 5 sec read zone. However, the 0.5-sec RLU value has a combination of both doped TAR and N-Phe beads. The calculated crossover of N-Phe signal into doped TAR window is about 0.57 times its 5 sec signal.

The results are summarized in Table 4 below.

TABLE 4

| | RNA Copies | | (WT) | (ELGA) |
|---|---|---|---|---|
| 0 | 88 | 61 | No | No |
| ELGA10$^5$/WT10$^2$ | 1758 | 1041 | Yes | Yes |
| ELGA10$^5$/WT10$^3$ | 67848 | 3122 | Yes | Yes |
| ELGA10$^5$/WT10$^4$ | 58844 | 2358 | Yes | Yes |
| ELGA10$^5$/WT10$^5$ | 29596 | 489 | Yes | Yes |
| ELGA10$^5$/WT0 | 2864 | 4607 | No | Yes |

All the positives and negatives were correctly identified.

Example 12

Homogenous Quantitative Detection of Wild-Type HIV and Quantitative Control (QA)

A probe specific for WT was attached to dopTAR beads. A probe specific for the Quantitative Control (QA) was attached to N-Phenyl Oxazine beads (chemiluminescer beads with 30 sec decay half-life). Sensitizer beads had attached thereto probes that recognize both WT and QA sequence. NASBA amplification was performed as described above but in the presence of 62.5 nM probe (4 different probes) and 1.25 µg of each type of bead (two chemiluminescer and two sensitizers). The 25 µL reaction was incubated for 90 min at 41° C. The signal was read and is tabulated below in Table 5. Read Cycle: 0.1 sec irradiation, 0.5 sec read; 30 sec delay and 5 sec read.

From raw signal the 5 sec window exhibited chemiluminescence from n-Phenyl Oxazine beads only. This could only occur when doped TAR beads were used since the decay is monophasic. When undoped TAR beads were used, the signal spills over into the 5 sec read zone. However, the 0.5-sec RLU value has a combination of both doped TAR and N-Phe beads. The calculated crossover of N-Phe signal into doped TAR window is about 0.57 times its 5 sec signal.

Wild-Type signal (0.5 second read): 400 RLU/10 attomoles

Quantitative control (QA) signal (5 second read): 20 RLU/10 attomoles.

TABLE 5

| | Corrected signal | | Relative attomoles | | |
|---|---|---|---|---|---|
| RNA Copies | 0.5 sec read | 5 sec read | (WT) | (QA) | WT/QA |
| WT 10$^2$ | 1640 | 2 | 40 | 1 | 40 |
| WT 10$^3$ | 16364 | 3 | 400 | 1 | 400 |
| QA 10$^3$ | 20 | 300 | 0.5 | 150 | 0.003 |
| QA 10$^4$ | 20 | 2760 | 0.5 | 1380 | 0.00036 |
| WT/QA 10$^2$/10$^3$ | 743 | 1655 | 19 | 820 | 0.023 |
| WT/QA 10$^2$/10$^5$ | 20 | 2501 | 0.5 | 1250 | 0.0004 |
| WT/QA 10$^3$/10$^3$ | 50403 | 2577 | 1260 | 1288 | 0.98 |
| WT/QA 10$^3$/10$^5$ | 707 | 3034 | 17.6 | 1517 | 0.0116 |

Example 13

Target HIV RNA (obtained from Organon Teknika, Boxtel, Netherlands) was amplified by the isothermal NASBA amplification procedure. The NASBA amplification kit of Organon Teknika was employed. Target RNA, referred to below as WT) at various initial input (number of molecules per reaction) was amplified in the presence of reference RNA, at known number of molecules. The reference RNA molecules, referred to below as $Q_a$) were engineered (by Organon Teknika) to be homologous to the target RNA except for an internal sequence of 21 nucleotides. This sequence in the reference RNA was 63 nucleotides from the 3'-end thereof and was complementary to the sequence in the third oligonucleotide probe set forth below. The corresponding sequence in the target RNA was complementary to the sequence in the second oligonucleotide probe set forth below. A sequence in both the target and reference RNA that was 29 nucleotides from the 3' end was complementary to a sequence in the first oligonucleotide probe or common probe.

The above design of the reference RNA ensures amplification of the reference and target RNA by the same NASBA primers and enzyme at equal amplification efficiency for target and reference RNA. The sequence of the target and reference RNA was as described by the manufacturer in *J. Virological Methods* (1993) 43:177–188.

A homogenous chemiluminescence detection method as described above was used to generate signals for determination. Chemiluminescence signal was produced when a pair of probes became bound to the target RNA analyte, one of which was bound to a singlet oxygen-producing particle, the sensitizer particle, and the other of which was bound to a particle dyed with a specific acceptor dye. These probes are referred to herein as particle detection probes. The particle detection probes included a first oligonucleotide detection probe that comprised a sequence that was complementary to a sequence in the first oligonucleotide probe indicated by underlining in the sequence below. A particle with which a sensitizer was associated was attached at the 3'-end of the first oligonucleotide detection probe. A second oligonucleotide detection probe comprised a sequence that was complementary to a sequence in the second oligonucleotide probe indicated by underlining in the sequence below. DopTAR dyed particles were attached at the 3'-end of the second oligonucleotide detection probe. A third oligonucleotide detection probe comprised a sequence that was complementary to a sequence in the third oligonucleotide probe indicated by underlining in the sequence below. N-PHE dyed particles were attached at the 3'-end of the third oligonucleotide detection probe. The particle detection probes became bound to the respective first, second or third oligonucleotide probes used in this example, where the binding was non-covalent and based on the hybridization of a sequence of the particle detection probes, either a 3'- or 5'-oligonucleotide tail, to a complementary sequence in the respective first, second or third oligonucleotide probes. Chemiluminescence signals produced by complexes of the common sensitizer particle, with each of the specific chemiluminescer particles, were specifically detected.

```
First oligonucleotide probe:
5'(dT)20TGTTAAAAGAGACCATCAATGAGGA3'    (SEQ ID NO:1)

Second oligonucleotide probe:
5'(TACT)5GCTGCAGAATGGGATAGA3'          (SEQ ID NO:2)

Third oligonucleotide probe:
5'GATGACAGTCGCATGCAG(CTAT)53'          (SEQ ID NO:3)
```

All probes were 3'-C7amino blocked and gel-purified by the manufacturer. The underlined portions of the probes represents the sequences of 20 nucleotides that are complementary to the 3'- or 5' tails on the particle detection probes.

RNA amplification of the test and reference RNA was carried out in mixtures containing all probes, detection particles and amplification reagents. The amplification reagents used were provided by the manufacturer (Organon Teknika). The lyophilized NASBA reagent Accusphere® was reconstituted as directed. The reagent mixture includes all primers, NTP's, $MgCl_2$ and buffer components. The target and reference RNA, the first, second and third oligonucleotide probes and corresponding particle detection probes were added to the reconstituted reaction mixture. The concentration of the first oligonucleotide probe was 25 nM and the concentration of the second and third oligonucleotide probes were at final concentration of 25 nM. The concentration of the particle detection probes was at final concentration of 1 μg particles per reaction. Target and reference RNA molecules, at known number of molecules, were added (2 μL) to the corresponding amplification tubes. The total volume of the initial reaction mixtures, including the target and reference RNA, was 15 μL. The mixtures were overlaid with 20 μL of white, light mineral oil (Aldrich Chemical Company) and incubated at 65° C. for 5 min. Following incubation at 41° C. for 10 min., the mixture of enzymes (5 μL from Organon Teknika) was added. Amplification was carried for a combined total of 70 min. primarily at a temperature of 41° C. However, 30 min. into this period, the temperature inadvertently dropped to 28° C. for a period of 8 min. until it was brought back to 41° C. for the remaining 32 min. All incubations were carried out in a thermocycler (Biometra Trio Thermocycler, Biometra). This thermocycler was employed because of the fact that it is a good incubation device, not because of the need for thermocylcing. At the end of the amplification reaction, the signal was read using a manual reader equipped with a filter wheel. Chemiluminescence signal read cycle was as follows: 3 cycles of 1 sec. Illumination at 680 nm, 0.5 sec read (550–660 nm), 30-sec. delay and 10 sec. read (650 nm short pass filter).

The results are summarized in Table 6 below. The Corrected chemiluminescence signals for the DopTAR and N-PHE particles are designated WT and QA respectively, and are given in the Table 6. The ratio of the corrected signals is proportional to and therefore representative of the ratio of test and reference RNA targets concentrations, as shown in Table 1.

TABLE 6

| RNA concentrations (pM) | | Corrected Signals Ration | | Conc. Ratio | Signal ratio |
|---|---|---|---|---|---|
| Test RNA | Ref. RNA | WT | Qa | Test/Reference | WT/Qa |
| 5 | 5 | 671 | 729 | 1 | 0.92 |
| 5 | 5 | 714 | 652 | 1 | 1.09 |
| 0.5 | 5 | 155 | 1728 | 0.1 | 0.09 |
| 0.5 | 5 | 362 | 1687 | 0.1 | 0.21 |
| 0.5 | 0.5 | 646 | 574 | 1 | 1.13 |
| 0.5 | 0.5 | 666 | 470 | 1 | 1.42 |

Example 14

Alternative Preparation of DopTar Particles

Particles comprising C-28 thioxene (prepared as described above), 1-chloro-9,10-bis(phenylethynyl)anthracene (1-Cl-BPEA) (from Aldrich Chemical Company) and rubrene (from Aldrich Chemical Company) were prepared as described above. An aliquot of the above particles (47.9 mg/1 ml 10% aqueous ethanol (pH 10–11) was diluted into 1 ml 10% aqueous ethanol in a 13×100 mm glass culture tube and placed in a heat block maintained at about 98 to 99° C. N-Heptadecylbenzene (as dopant) (HB) (20 µl) (Pfaltz and Bauer) was diluted into 2 ml ethanol in a similar tube and placed in the heat block. A few minutes were allowed for equilibration and then the particles were rapidly added to the HB solution by Pasteur pipette. The contents were thoroughly mixed by pipette for 20 minutes. The contents of the tube were cooled and 2 ml of ethanol was added to the mixture to bring the concentration to 67%. Aliquots of the suspension were placed into 6×1.5-ml eppendorf tubes and centrifuged at 15 k rpm for 20 minutes in the benchtop refrigerated centrifuge. Approximately 5.5 ml of clear but visibly yellow supernatant was removed from the particles, which were suspended in 0.5 ml 50% ethanol by sonication. After centrifugation at 15 k rpm for 20 minutes, the supernatant was removed and the pellets were suspended in 2 ml 25% ethanol.

A 100 µl aliquot from the original particle (TAR) suspension and a 100 µl aliquot from the particle suspension containing the dopant (DopTAR particles) as described above were placed in weighed glass tubes and evaporated to a constant weight of 5.5 and 2.7 mg, respectively. The dry residues were dissolved in 8 and 4 ml dioxane, respectively. The absorption spectra of these solutions were compared. A reduction of approximately 15% in the absorption spectra of the DopTAR material suggests that approximately 15% of the weight of the particle weight is due to the presence of HB.

The chemiluminescent decay of the TAR and DopTAR particles was compared. Each type of particle (1 mg) was diluted into 1 ml soluble sensitizer, namely, aluminum phthalocyanine tetrasulfonate (Porphyrin Products, Logan, Utah) (O.D. 0.56 @ 678 nm) in water. The mixtures were equilibrated at 37° C. using the following parameters: illumination 1 sec. read 30 sec., 200 data points per cycle. At 5 seconds the emission from the DopTAR particles dropped to about 0.2% whereas the emission from the original TAR particles dropped to about 4% and by 10 sec. The DopTAR particles reached background whereas the original TAR particles were still emitting about 1.5% of their initial intensity.

The size distribution of the starting TAR particles and the DopTAR particles were compared by a NICOMP submicron particle sizer Model 370 (NICOMP) Particle Sizing Systems, Santa Barbara, Calif.). Each type of particle (20 µg) was present in 1 ml 0.2 micron filtered D.I. water. The mean diameter of the DopTAR particles was about 25 nm larger than the starting TAR particles, about 220 versus 195, respectively.

The chemiluminescent emission spectra of the DopTAR particles was compared to the starting particle by diluting 0.5 mg particles into 0.5 ml soluble sensitizer (O.D. 1.12 @ 678 nm) and freezing in dry ice. The frozen suspension was then illuminated for 60 sec. with a Dolan-Jenner lamp fitted with a 650 nm long pass filter. Following illumination, the sample was immediately transferred to the fluorometer and the chemiluminescent emission recorded in luminescence mode (Em slit 20 nm, scan speed 1200 nm/min). A minor emission from thioxene (420) in the starting particles was reduced in the DopTAR particles. Except for that minor difference the two spectra were nearly identical indicating that incorporation of dopant (doping) has had no effect on the emission spectra of the particles.

The above discussion includes certain theories as to mechanisms involved in the present invention. These theories should not be construed to limit the present invention in any way, since it has been demonstrated that the present invention achieves the results described.

Although the foregoing invention has been described in some detail by way of illustration and example for purposes of clarity and understanding, it will be obvious that certain changes or modifications may be practiced within the scope of the appended claims.

The invention claimed is:

1. A method for determining the presence or amount of an analyte, said method comprising:
   (a) providing in combination (1) a medium suspected of containing said analyte, and (2) a first specific binding pair (sbp) member capable of binding to said analyte or to a second sbp member to form a complex related to the presence of said analyte, wherein at least one of said sbp members is bound to polymeric particles of about 20 nm to about 100 µm in diameter having homogeneously dispersed therein about 1 to about 20 weight percent of a dopant, which is a plasticizer selected from the group consisting of higher alkylaromatic compounds and higher alkyloxyaromatic compounds and fluorocarbons, a photosensitizer and a chemiluminescent substance,
   (b) activating said chemiluminescent substance and
   (c) determining the effect of said activating on the optical properties of said combination, the magnitude of said effect being related to the presence or amount of said analyte in said medium.

2. The method of claim 1 wherein said first sbp member is associated with said particles.

3. The method of claim 1 wherein said combination comprises said second sbp member associated with said particles.

4. The method of claim 1 wherein said photosensitizer is incorporated into a second set of particles associated with one of said sbp members.

5. The method of claim 4 wherein said second set of particles comprises a dopant.

6. The method of claim 1 wherein said polymeric particles comprise a polymer selected from the group consisting of polystyrenes, polyvinyl chlorides and polyvinylnaphthalenes.

7. A method for determining the presence or amount of an analyte, said method comprising:
   (a) combining a sample suspected of containing said analyte with polymeric particles of 20 nm to 100 µm in diameter having dissolved therein (a) 2 to 10% by weight of a dopant, which is a plasticizer selected from the group consisting of higher alkylaromatic compounds and higher alkyloxyaromatic compounds and fluorocarbons, (b) a photosensitizer and (c) a chemiluminescent substance and reagents that produce a color change in relation to the amount of said analyte and
   (b) activating said photoactive substance and relating the intensity of the light emitted to the amount of said color change, the amount thereof being related to the presence or amount of said analyte.

\* \* \* \* \*

SEQUENCE LISTING

```
<160> NUMBER OF SEQ ID NOS: 3

<210> SEQ ID NO 1
<211> LENGTH: 45
<212> TYPE: DNA
<213> ORGANISM: Artificial Sequence
<220> FEATURE:
<223> OTHER INFORMATION: Oligonucleotide Probe

<400> SEQUENCE: 1 ttttttttt tttttttttt tgttaaaaga gaccatcaat gagga            45

<210> SEQ ID NO 2
<211> LENGTH: 38
<212> TYPE: DNA
<213> ORGANISM: Artificial Sequence
<220> FEATURE:
<223> OTHER INFORMATION: Oligonucleotide Probe

<400> SEQUENCE: 2
tacttactta cttacttact gctgcagaat gggataga                   38

<210> SEQ ID NO 3
```

-continued

```
<211> LENGTH: 38
<212> TYPE: DNA
<213> ORGANISM: Artificial Sequence
<220> FEATURE:
<223> OTHER INFORMATION: Oligonucleotide Probe

<400> SEQUENCE: 3
gatgacagtc gcatgcagct atctatctat ctatctat                              38
```